(12) United States Patent
Jalinot et al.

(10) Patent No.: US 7,709,606 B2
(45) Date of Patent: May 4, 2010

(54) INTERACTING POLYPEPTIDE COMPRISING A HEPTAPEPTIDE PATTERN AND A CELLULAR PENETRATION DOMAIN

(75) Inventors: Pierre Jalinot, Sainte Foy-les-Lyon (FR); Armelle Roison, Clonas-sur-Vareze (FR); Jean-Philippe Robin, Lyons (FR)

(73) Assignees: Ecole Normale Superieure de Lyon, Lyons (FR); Centre National de la Recherche Scientifique, Paris (FR)

( * ) Notice: Subject to any disclaimer, the term of this patent is extended or adjusted under 35 U.S.C. 154(b) by 237 days.

(21) Appl. No.: 11/396,196

(22) Filed: Mar. 30, 2006

(65) Prior Publication Data

US 2006/0240516 A1     Oct. 26, 2006

Related U.S. Application Data

(63) Continuation of application No. PCT/FR2004/002479, filed on Sep. 30, 2004.

(30) Foreign Application Priority Data

Sep. 30, 2003  (FR)  ................................... 03 11463

(51) Int. Cl.
  *C07K 14/00*  (2006.01)
(52) U.S. Cl. .................................................. 530/350
(58) Field of Classification Search .................. None
  See application file for complete search history.

(56) References Cited

U.S. PATENT DOCUMENTS

| 6,420,518 B1 | 7/2002 | Chen et al. | |
| 6,747,135 B1 * | 6/2004 | Nolan et al. | 530/408 |
| 2005/0108791 A1 * | 5/2005 | Edgerton | 800/284 |

FOREIGN PATENT DOCUMENTS

| EP | 1033401 | * | 6/2000 |
| EP | 1243595 A1 | | 9/2002 |
| WO | WO 96/23899 | | 8/1996 |
| WO | WO 02/34291 | | 5/2002 |
| WO | WO 03/035697 | | 5/2003 |

OTHER PUBLICATIONS

Xia et al., The HIV Tat protein transduction domain improves the biodistribution of β-glucuronidase expressed from recombinant viral vectors, Nature Biotechnology, 2001, 19:640-644.*
Li et al., Correlation between hydrophobic properties and efficiency of carrier-mediated membrane transduction and apoptosis of a p53 C-terminal peptide, Biochemical and Biophysical Research Communications, 2002, 298:439-449.*
Tasciotti et al., Transcellular transfer of active HSV-1 thymidine kinase mediated by an 11-amino-acid peptide from HIV-1 Tat, Cancer Gene Therapy, 2003, 10:64-74.*
Chuang et al., Pharmaceutical Strategies Utilizing Recombinant Human Serum Albumin, Pharmaceutical Research, 2002, 19(5):569-577.*
EP1033401 Sequence Search Results.*
Luo, Y. et al., (1994) "Cellular Protein Modulates Effects of Human Immunodeficiency Virus Type 1 Rev," Journal of Virology, 68(6): 3850-3856.
Duprez, E. et al., (1999) "SUMO-1 Modification of the Acute Promyelocytic Leukaemia Protein PML: Implications for Nuclear Localisation," Journal of Cell Science, 112: 381-393.
Fields, S. et al., (1994) "The Two-Hybrid System: An Assay for Protein-Protein Interactions," Falstrom Flex-I-Touch for TIG ARC Welding, 10(8): 286-292.
Roisin, A. et al., (2004) "Inhibition of HIV-1 Replication by Cell-penetrating Peptides," Journal of Biological Chemistry, 279(10): 9208-9214.
Ptak, R.G. et al., (2002) "HIV-1 Regulatory Proteins: Targets for Novel Drug Development," Expert Opinion on Investigational Drugs, 11(8): 1099-1115.
Nakaya, T. et al., (1997) "Inhibition of HIV-1 Replication by Targeting The Rev Protein," Official Journal of the Leukemia Society of America, 11: 134-137.
Veschambre, P. et al., (1995) "Evidence for Functional Interaction between the HIV-1 Tat Transactivator and the TATA Box Binding Protein in Vivo," Journal of Molecular Biology, 250: 169-180.
Wender, P.A. et al., (2000) "The Design, Synthesis, and Evaluation of Molecules That Enable or Enhance Cellular Uptake: Peptoid Molecular Transporters," PNAS, 97(24): 13003-13008.
Farjot, G. et al., (1999) "A New Nucleoporin-like Protein Interacts with Both HIV-1 Rev Nuclear Export Signal and CRM-1," Journal of Biological Chemistry, 274(24): 17309-17317.
Desbois, C. et al., (1996) "Exclusion of Int-6 from PML Nuclear Bodies by Binding to the HTLV-I Tax Oncoprotein," Science, 273: 951-953.

* cited by examiner

*Primary Examiner*—Stacy B. Chen
*Assistant Examiner*—Nicole Kinsey White
(74) *Attorney, Agent, or Firm*—John P. White; Cooper & Dunham LLP

(57) ABSTRACT

The invention relates to an interacting polypeptide consisting of or comprising a heptapeptide pattern of sequence $X_1X_2X_3X_4X_5X_6X_7$ and a transduction domain, characterized in that it is a chimera polypeptide, the amino acid $X_7$ is located between 5 and 35 amino acids of the C-terminal end of said polypeptide, and that the domain (b) is situated in C-terminal relative to pattern (a). The invention also relates to screening methods for identifying interacting polypeptides capable of modifying the phenotype of a cell and to uses of interacting polypeptides as mentioned in phenotypic screens or for therapeutic purposes. Lastly, the invention concerns interacting polypeptides capable of modifying the function of the HIV-1 Rev viral protein.

19 Claims, 15 Drawing Sheets

Step 1: Yeast screening of a random heptapeptide library against the targeted protein:
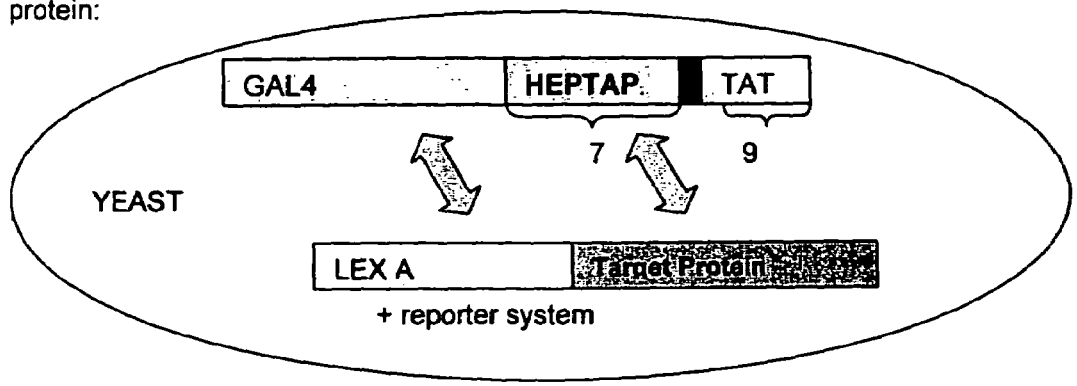
Step 2: Verification of the existence of an interaction in mammalian cells:
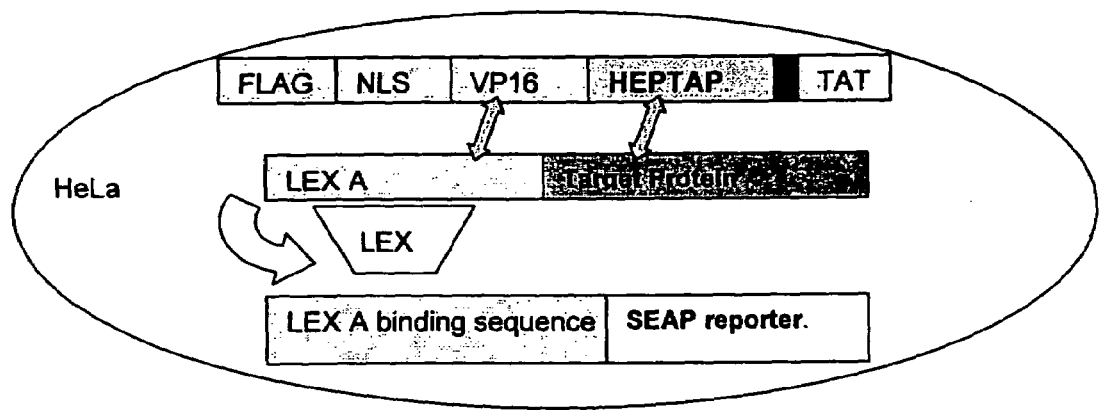
Step 3: Functional tests
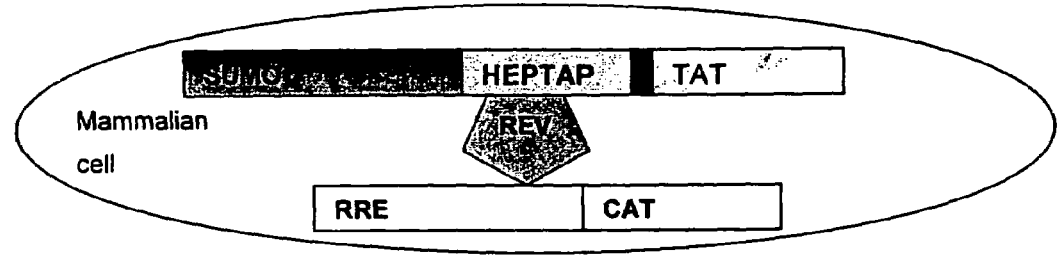
Step 4: Mass production
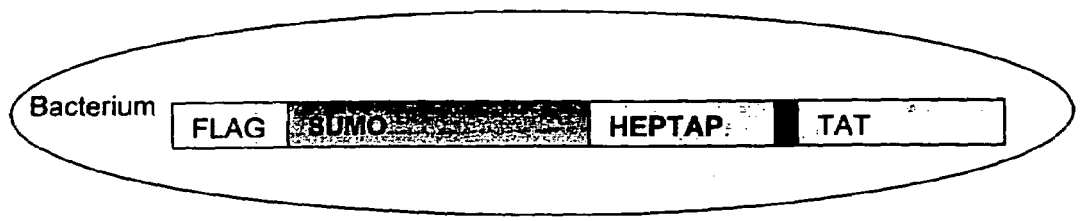
FIGURE 1

Figure 2A:
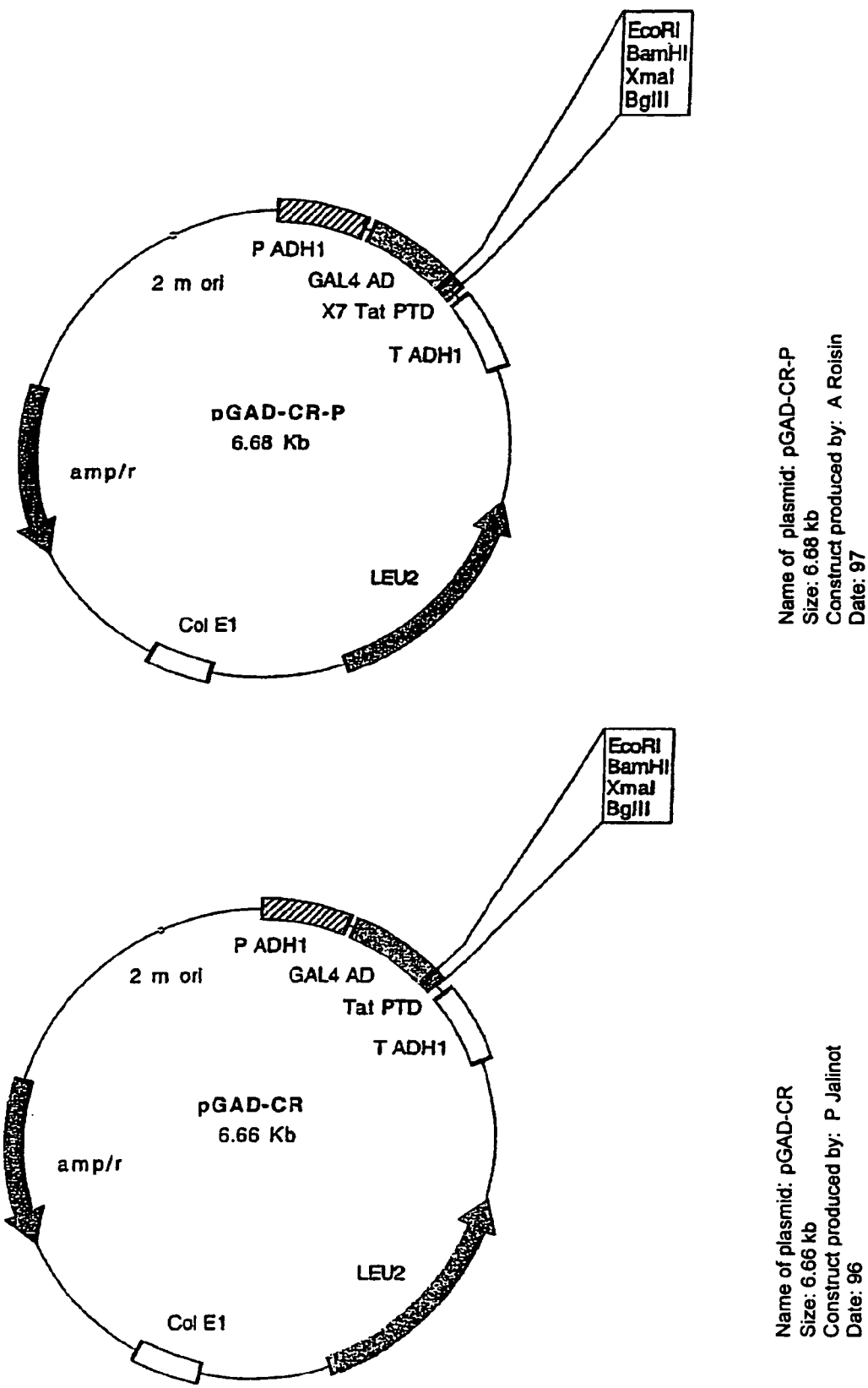

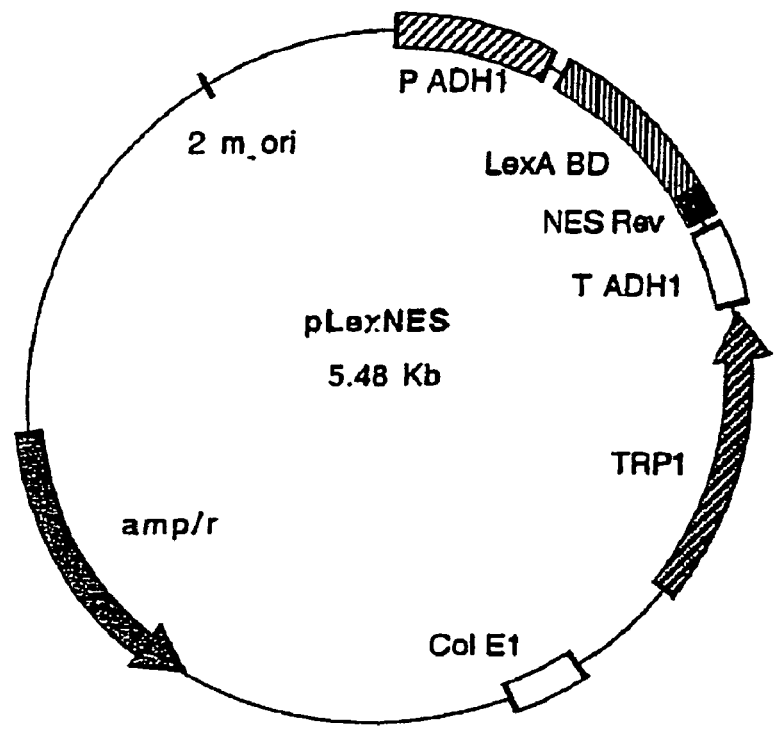
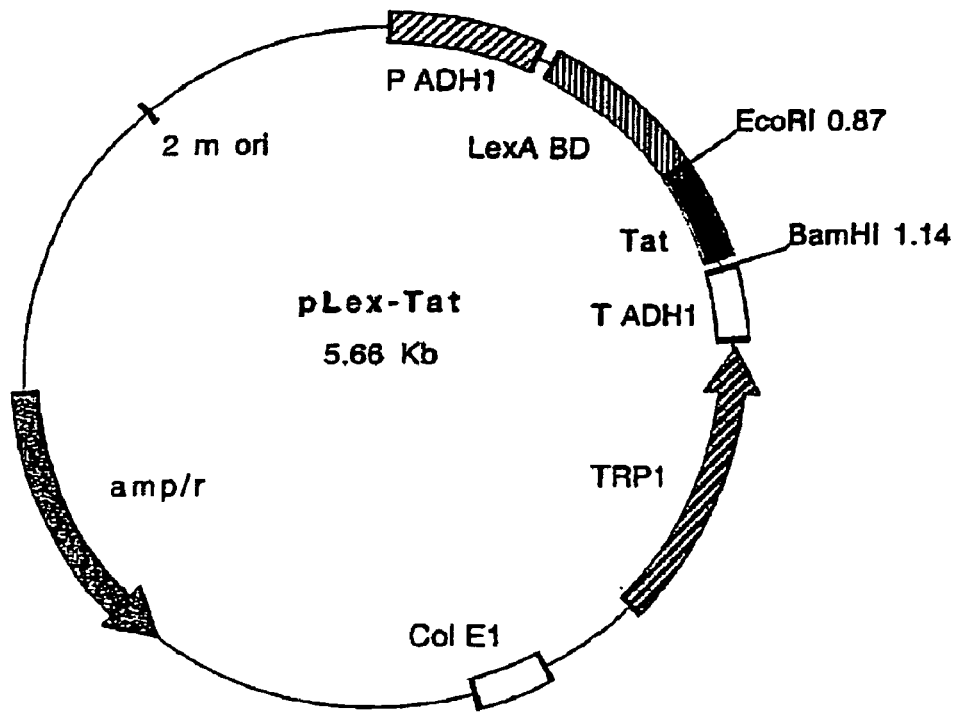
FIGURE 2B

Figure 3B:
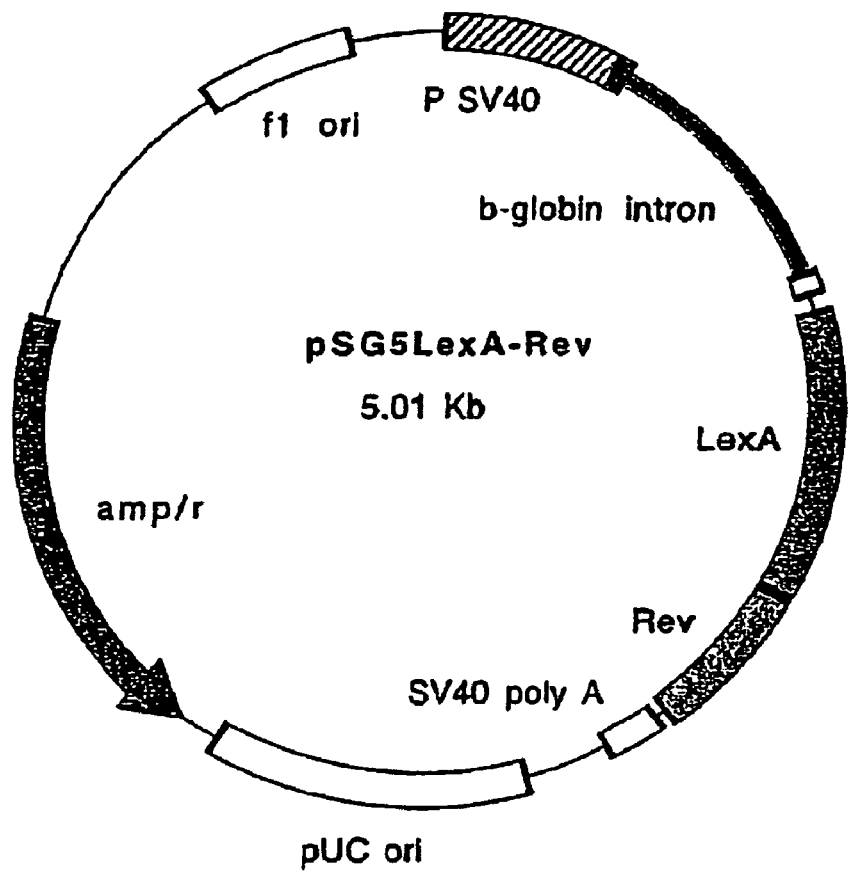

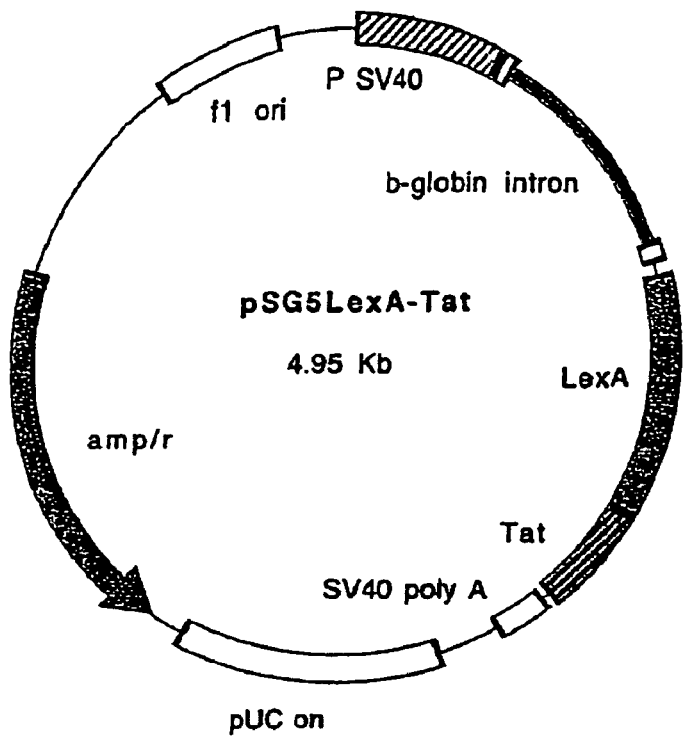
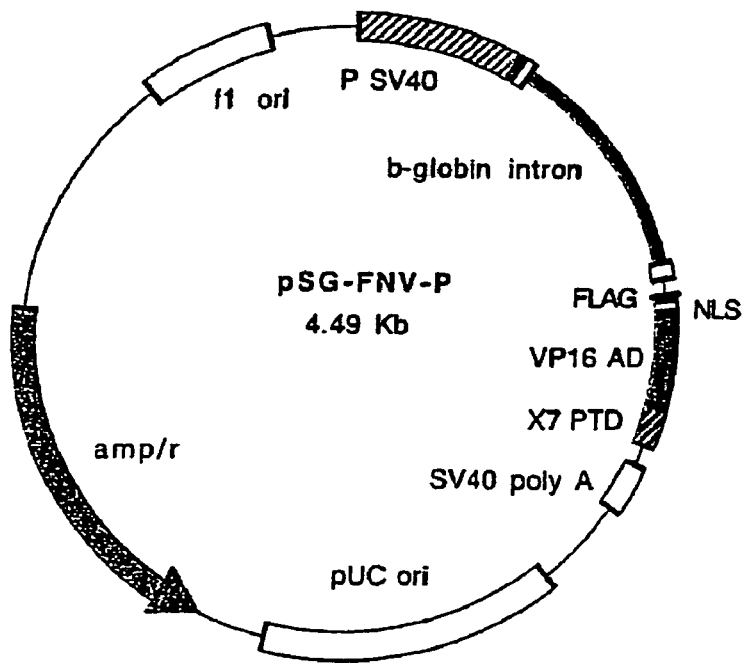
FIGURE 3A

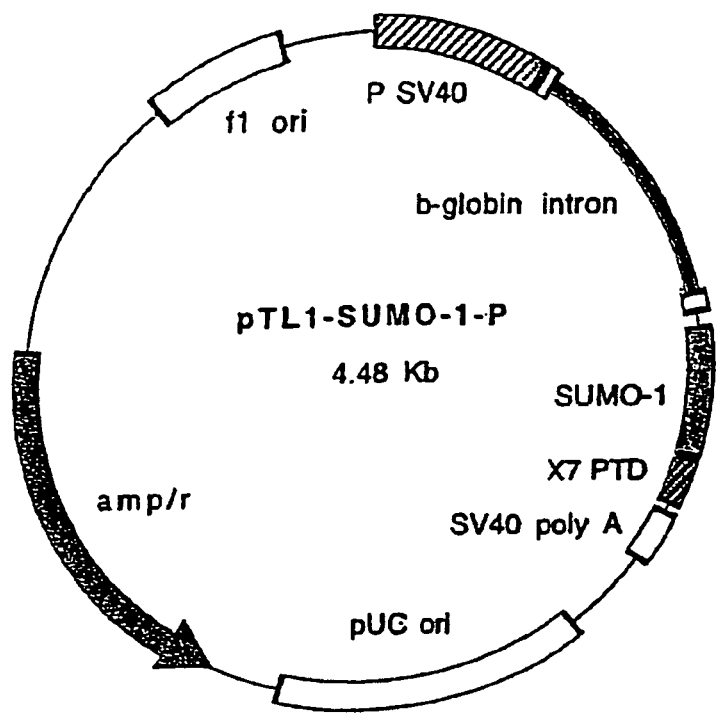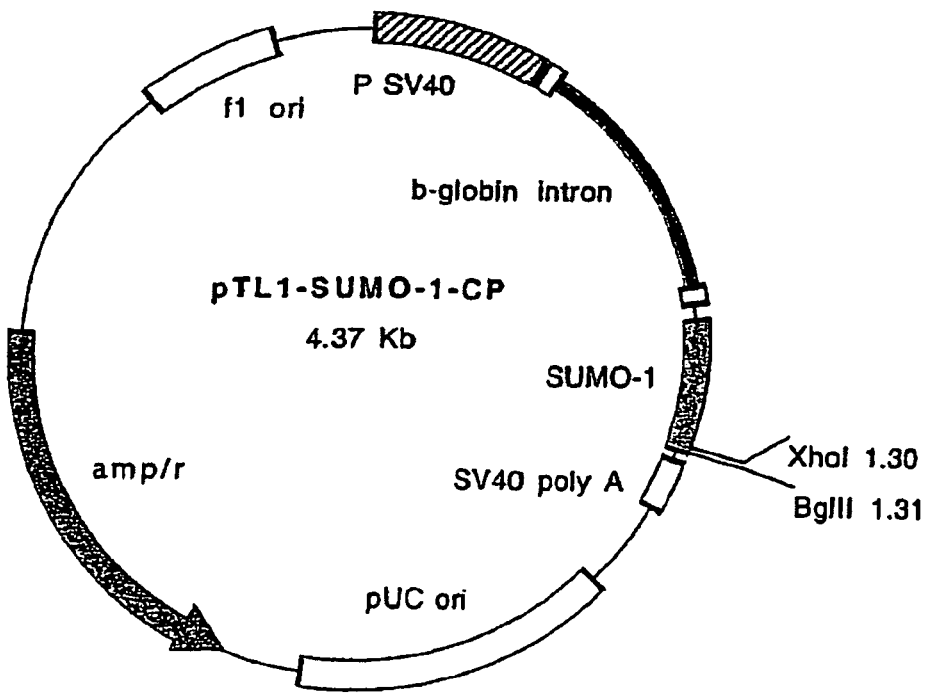
FIGURE 4

1- SUMO-1 wild type (Homo sapiens)
2- SUMO Interacting peptide (SHP)

1 - MSDQEAKPSTEDLGDKKEGEYIKLKVIGQDSSEIHFKVKMTTHLKKLKESYCQRQGVPMNSLRFLFEGQRIADN
    *************************************************************************
2 - MSDQEAKPSTEDLGDKKEGEYIKLKVIGQDSSEIHFKVKMTTHLKKLKESYCQRQGVPMNSLRFLFEGQRIADN

1 - HTPKELGMEEEDVIEVYQEQTGGHSTV
    ***********************
2 - HTPKELGMEEEDVIEVYQEQTARPPNPKKEIELGGGGSXXXXXXXPGRKKRRQRRRG

1- Ubiquitin (Homo sapiens)
2- Ub Interacting peptide

3 - MQIFVKTLTGKTITLEVEPSDTIENVKAKIQDKEGIPPDQQRLIFAGKQLEDGRTLSDYNIQKESTLHLVLRLR
    *************************************************************************
4 - MQIFVKTLTGKTITLEVEPSDTIENVKAKIQDKEGIPPDQQRLIFAGKQLEDGRTLSDYNIQKESTLHLVLRLR

3 - GG

4 - ARPPNPKKEIELGGGGSXXXXXXXPGRKKRRQRRRG

FIGURE 6

A
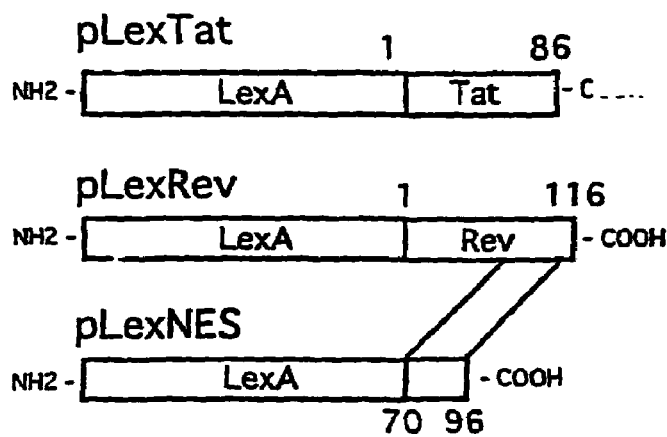
B pGAD-CR-P
C pSG-FNV-P
FIGURE 7

SEQUENCE LISTING

```
<160> NUMBER OF SEQ ID NOS: 80

<210> SEQ ID NO 1
<211> LENGTH: 95
<212> TYPE: PRT
<213> ORGANISM: Homo sapiens

<400> SEQUENCE: 1

Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45

Glu Ser Tyr Cys Gln Arg Gln Gly Val Pro Met Asn Ser Leu Arg Phe
    50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr
                85                  90                  95

<210> SEQ ID NO 2
<211> LENGTH: 7
<212> TYPE: PRT
<213> ORGANISM: Artificial Sequence
<220> FEATURE:
<223> OTHER INFORMATION: Chemically synthesized

<400> SEQUENCE: 2

Phe Trp Phe Cys Gly Leu Lys
1               5

<210> SEQ ID NO 3
<211> LENGTH: 7
<212> TYPE: PRT
<213> ORGANISM: Artificial Sequence
<220> FEATURE:
<223> OTHER INFORMATION: Chemically synthesized
```

```
<400> SEQUENCE: 3

Asn Trp Leu Cys Cys Leu Asn
1               5

<210> SEQ ID NO 4
<211> LENGTH: 19
<212> TYPE: PRT
<213> ORGANISM: Artificial Sequence
<220> FEATURE:
<223> OTHER INFORMATION: Chemically synthesized

<400> SEQUENCE: 4

Phe Trp Phe Cys Gly Leu Lys Pro Gly Arg Lys Lys Arg Arg Gln Arg
1               5                   10                  15

Arg Arg Gly

<210> SEQ ID NO 5
<211> LENGTH: 19
<212> TYPE: PRT
<213> ORGANISM: Artificial Sequence
<220> FEATURE:
<223> OTHER INFORMATION: Chemically synthesized

<400> SEQUENCE: 5

Asn Trp Leu Cys Cys Leu Asn Pro Gly Arg Lys Lys Arg Arg Gln Arg
1               5                   10                  15

Arg Arg Gly

<210> SEQ ID NO 6
<211> LENGTH: 18
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(7)
<223> OTHER INFORMATION: Amino acids at positions 1, 2, 3, 4, 5, 6 and 7
      are Xaa wherein Xaa: any amino acid.

<400> SEQUENCE: 6

Xaa Xaa Xaa Xaa Xaa Xaa Xaa Pro Gly Lys Lys Arg Arg Gln Arg Arg
1               5                   10                  15

Arg Gly

<210> SEQ ID NO 7
<211> LENGTH: 130
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (113)..(119)
<223> OTHER INFORMATION: Amino acids at positions 113, 114, 115, 116,
      117, 118 and 119 are Xaa wherein Xaa: any amino acid.

<400> SEQUENCE: 7

Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
                20                  25                  30

Glu Ile His Phe Lys Val Lys Met Thr Thr His Leu Lys Lys Leu Lys
            35                  40                  45
```

-continued

```
Glu Ser Tyr Cys Gln Arg Gln Gly Val Pro Met Asn Ser Leu Arg Phe
 50                  55                  60

Leu Phe Glu Gly Gln Arg Ile Ala Asp Asn His Thr Pro Lys Glu Leu
 65                  70                  75                  80

Gly Met Glu Glu Glu Asp Val Ile Glu Val Tyr Gln Glu Gln Thr Ala
                 85                  90                  95

Arg Pro Pro Asn Pro Lys Lys Glu Ile Glu Leu Gly Gly Gly Gly Ser
                100                 105                 110

Xaa Xaa Xaa Xaa Xaa Xaa Xaa Pro Gly Lys Lys Arg Arg Gln Arg Arg
            115                 120                 125

Arg Gly
    130

<210> SEQ ID NO 8
<211> LENGTH: 12
<212> TYPE: PRT
<213> ORGANISM: Human immunodeficiency virus

<400> SEQUENCE: 8

Leu Gln Leu Pro Pro Leu Glu Arg Leu Thr Leu Asp
 1               5                   10

<210> SEQ ID NO 9
<211> LENGTH: 9
<212> TYPE: PRT
<213> ORGANISM: Human immunodeficiency virus

<400> SEQUENCE: 9

Arg Lys Lys Arg Arg Gln Arg Arg Arg
 1               5

<210> SEQ ID NO 10
<211> LENGTH: 7
<212> TYPE: PRT
<213> ORGANISM: Artificial Sequence
<220> FEATURE:
<223> OTHER INFORMATION: Chemically synthesized

<400> SEQUENCE: 10

Lys Leu Gly Cys Phe Trp Phe
 1               5

<210> SEQ ID NO 11
<211> LENGTH: 7
<212> TYPE: PRT
<213> ORGANISM: Artificial Sequence
<220> FEATURE:
<223> OTHER INFORMATION: Chemically synthesized

<400> SEQUENCE: 11

Asn Leu Cys Cys Leu Trp Asn
 1               5

<210> SEQ ID NO 12
<211> LENGTH: 11
<212> TYPE: PRT
<213> ORGANISM: Artificial Sequence
<220> FEATURE:
<223> OTHER INFORMATION: Chemically synthesized
```

```
<400> SEQUENCE: 12

Pro Gly Arg Lys Lys Arg Arg Gln Arg Arg
1               5                   10

<210> SEQ ID NO 13
<211> LENGTH: 110
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (92)..(98)
<223> OTHER INFORMATION: Amino acids at positions 92, 93, 94, 95, 96, 97
      and 98 are Xaa wherein Xaa: any amino acid.

<400> SEQUENCE: 13

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Ala Arg Pro Pro Asn Pro
65                  70                  75                  80

Lys Lys Glu Ile Glu Leu Gly Gly Gly Ser Xaa Xaa Xaa Xaa Xaa
                85                  90                  95

Xaa Xaa Pro Gly Arg Lys Lys Arg Arg Gln Arg Arg Gly
            100                 105                 110

<210> SEQ ID NO 14
<211> LENGTH: 76
<212> TYPE: PRT
<213> ORGANISM: Homo sapiens

<400> SEQUENCE: 14

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 15
<211> LENGTH: 74
<212> TYPE: PRT
<213> ORGANISM: Homo sapiens

<400> SEQUENCE: 15

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30
```

```
Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg
65                  70

<210> SEQ ID NO 16
<211> LENGTH: 112
<212> TYPE: PRT
<213> ORGANISM: Artificial Sequence
<220> FEATURE:
<223> OTHER INFORMATION: Chemically synthesized

<400> SEQUENCE: 16

Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45

Glu Ser Tyr Cys Gln Arg Gln Gly Val Pro Met Asn Ser Leu Arg Phe
    50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr Ala
                85                  90                  95

Arg Pro Pro Asn Pro Lys Lys Glu Ile Glu Leu Gly Gly Gly Gly Ser
            100                 105                 110

<210> SEQ ID NO 17
<211> LENGTH: 64
<212> TYPE: DNA
<213> ORGANISM: Artificial
<220> FEATURE:
<223> OTHER INFORMATION: Primer

<400> SEQUENCE: 17
aattgggtgg tggcggatcc ggtttgcccg ggagaaagaa gcgtagacaa agaagacgtg    60
gtta                                                                64

<210> SEQ ID NO 18
<211> LENGTH: 65
<212> TYPE: DNA
<213> ORGANISM: Artificial
<220> FEATURE:
<223> OTHER INFORMATION: Primer

<400> SEQUENCE: 18
cccaccaccg cctaggccaa acgggccctc tttcttcgca tctgtttctt ctgcaccaat    60
tctag                                                               65

<210> SEQ ID NO 19
<211> LENGTH: 46
<212> TYPE: DNA
<213> ORGANISM: Artificial
<220> FEATURE:
<223> OTHER INFORMATION: Primer
```

```
<220> FEATURE:
<221> NAME/KEY: misc_feature
<222> LOCATION: (11)..(31)
<223> OTHER INFORMATION: Nucleotides at positions 11, 12, 13, 14, 15,
      16, 17, 18, 19, 20, 21, 22, 23, 24, 25, 26, 27, 28, 29, 30 and 31
      are n wherein n: any nucleotide

<400> SEQUENCE: 19
actcggatcc nnnnnnnnnn nnnnnnnnnn ncccggggtc gcagtg                    46

<210> SEQ ID NO 20
<211> LENGTH: 14
<212> TYPE: DNA
<213> ORGANISM: Artificial
<220> FEATURE:
<223> OTHER INFORMATION: Primer

<400> SEQUENCE: 20
ggccccagcg tcac                                                       14

<210> SEQ ID NO 21
<211> LENGTH: 10
<212> TYPE: PRT
<213> ORGANISM: Artificial Sequence
<220> FEATURE:
<223> OTHER INFORMATION: Chemically synthesized

<400> SEQUENCE: 21

Arg Arg Lys Ala Arg Arg Gln Arg Arg Arg
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Chemically synthesized

<400> SEQUENCE: 22

Arg Arg Arg Arg Arg Arg Arg
1               5

<210> SEQ ID NO 23
<211> LENGTH: 8
<212> TYPE: PRT
<213> ORGANISM: Artificial Sequence
<220> FEATURE:
<223> OTHER INFORMATION: Chemically synthesized

<400> SEQUENCE: 23

Arg Arg Arg Arg Arg Arg Arg Arg
1               5

<210> SEQ ID NO 24
<211> LENGTH: 9
<212> TYPE: PRT
<213> ORGANISM: Artificial Sequence
<220> FEATURE:
<223> OTHER INFORMATION: Chemically synthesized

<400> SEQUENCE: 24

Arg Arg Arg Arg Arg Arg Arg Arg Arg
1               5
```

```
<210> SEQ ID NO 25
<211> LENGTH: 7
<212> TYPE: PRT
<213> ORGANISM: Artificial Sequence
<220> FEATURE:
<223> OTHER INFORMATION: Chemically synthesized

<400> SEQUENCE: 25

Ala Trp Leu Cys Cys Leu Asn
1               5

<210> SEQ ID NO 26
<211> LENGTH: 7
<212> TYPE: PRT
<213> ORGANISM: Artificial Sequence
<220> FEATURE:
<223> OTHER INFORMATION: Chemically synthesized

<400> SEQUENCE: 26

Asn Trp Leu Cys Cys Leu Ala
1               5

<210> SEQ ID NO 27
<211> LENGTH: 7
<212> TYPE: PRT
<213> ORGANISM: Artificial Sequence
<220> FEATURE:
<223> OTHER INFORMATION: Chemically synthesized

<400> SEQUENCE: 27

Phe Trp Phe Cys Gly Leu Ala
1               5

<210> SEQ ID NO 28
<211> LENGTH: 4
<212> TYPE: PRT
<213> ORGANISM: Artificial Sequence
<220> FEATURE:
<223> OTHER INFORMATION: Chemically synthesized

<400> SEQUENCE: 28

Gly Gly Gly Gly
1

<210> SEQ ID NO 29
<211> LENGTH: 7
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Amino acid at position 1 is  Xaa wherein Xaa:
      any amino acid.
<220> FEATURE:
<221> NAME/KEY: MISC_FEATURE
<222> LOCATION: (3)..(3)
<223> OTHER INFORMATION: Amino acid at position 3 is  Xaa wherein Xaa:
      any amino acid.
<220> FEATURE:
<221> NAME/KEY: MISC_FEATURE
<222> LOCATION: (5)..(5)
<223> OTHER INFORMATION: Amino acid at position 5 is  Xaa wherein Xaa:
      any amino acid.
<220> FEATURE:
<221> NAME/KEY: MISC_FEATURE
<222> LOCATION: (7)..(7)
<223> OTHER INFORMATION: Amino acid at position 7 is  Xaa wherein Xaa:
      any amino acid.
```

```
<400> SEQUENCE: 29

Xaa Trp Xaa Cys Xaa Leu Xaa
1               5

<210> SEQ ID NO 30
<211> LENGTH: 31
<212> TYPE: DNA
<213> ORGANISM: Artificial
<220> FEATURE:
<223> OTHER INFORMATION: Primer

<400> SEQUENCE: 30
tgaaggtcga ccaccaaacc caaaaaaga g                              31

<210> SEQ ID NO 31
<211> LENGTH: 20
<212> TYPE: DNA
<213> ORGANISM: Artificial
<220> FEATURE:
<223> OTHER INFORMATION: Primer

<400> SEQUENCE: 31
cctgagaaag caacctgacc                                          20

<210> SEQ ID NO 32
<211> LENGTH: 30
<212> TYPE: DNA
<213> ORGANISM: Artificial
<220> FEATURE:
<223> OTHER INFORMATION: Primer

<400> SEQUENCE: 32
gggtcgacgt ccatatgtct gaccaggagg                               30

<210> SEQ ID NO 33
<211> LENGTH: 27
<212> TYPE: DNA
<213> ORGANISM: Artificial
<220> FEATURE:
<223> OTHER INFORMATION: Primer

<400> SEQUENCE: 33
aaaagatctc taaactgttg aatgacc                                  27

<210> SEQ ID NO 34
<211> LENGTH: 30
<212> TYPE: DNA
<213> ORGANISM: Artificial
<220> FEATURE:
<223> OTHER INFORMATION: Primer

<400> SEQUENCE: 34
gggtcgacgt ccatatgtct gaccaggagg                               30

<210> SEQ ID NO 35
<211> LENGTH: 38
<212> TYPE: DNA
<213> ORGANISM: Artificial
<220> FEATURE:
<223> OTHER INFORMATION: Primer

<400> SEQUENCE: 35
atcagatctg aatctcgagc cgtttgttcc tgataaac                      38
```

<210> SEQ ID NO 36
<211> LENGTH: 34
<212> TYPE: DNA
<213> ORGANISM: Artificial
<220> FEATURE:
<223> OTHER INFORMATION: Primer

<400> SEQUENCE: 36
ctaagaattc aaaatgcaaa tcttcgtgaa aacc                          34

<210> SEQ ID NO 37
<211> LENGTH: 37
<212> TYPE: DNA
<213> ORGANISM: Artificial
<220> FEATURE:
<223> OTHER INFORMATION: Primer

<400> SEQUENCE: 37
cacgaagatc tacactcgag ctctcagacg caggacc                       37

<210> SEQ ID NO 38
<211> LENGTH: 7
<212> TYPE: PRT
<213> ORGANISM: Artificial Sequence
<220> FEATURE:
<223> OTHER INFORMATION: Chemically synthesized

<400> SEQUENCE: 38

Phe Thr Met Arg Gly Val Asp
1               5

<210> SEQ ID NO 39
<211> LENGTH: 25
<212> TYPE: PRT
<213> ORGANISM: Artificial Sequence
<220> FEATURE:
<223> OTHER INFORMATION: Chemically synthesized

<400> SEQUENCE: 39

Ile Thr Arg Arg Ile Glu Met Pro Gly Arg Asp Ile Pro Gly Val Asp
1               5                   10                  15

Gly Ser Ile Leu Arg Gly Cys Trp Asp
            20                  25

<210> SEQ ID NO 40
<211> LENGTH: 7
<212> TYPE: PRT
<213> ORGANISM: Artificial Sequence
<220> FEATURE:
<223> OTHER INFORMATION: Chemically synthesized

<400> SEQUENCE: 40

Gly Ala Val Asp Lys Ser His
1               5

<210> SEQ ID NO 41
<211> LENGTH: 7
<212> TYPE: PRT
<213> ORGANISM: Artificial Sequence
<220> FEATURE:
<223> OTHER INFORMATION: Chemically synthesized

<400> SEQUENCE: 41

Ser Arg Val Asp Arg Lys Asp
1               5

<210> SEQ ID NO 42
<211> LENGTH: 7
<212> TYPE: PRT
<213> ORGANISM: Artificial Sequence
<220> FEATURE:
<223> OTHER INFORMATION: Chemically synthesized

<400> SEQUENCE: 42

Met Cys Val Asp Leu Leu Leu
1               5

<210> SEQ ID NO 43
<211> LENGTH: 7
<212> TYPE: PRT
<213> ORGANISM: Artificial Sequence
<220> FEATURE:
<223> OTHER INFORMATION: Chemically synthesized

<400> SEQUENCE: 43

Arg Gln Val Gly Met Leu Tyr
1               5

<210> SEQ ID NO 44
<211> LENGTH: 7
<212> TYPE: PRT
<213> ORGANISM: Artificial Sequence
<220> FEATURE:
<223> OTHER INFORMATION: Chemically synthesized

<400> SEQUENCE: 44

Leu Ala Pro Arg Asp Leu Leu
1               5

<210> SEQ ID NO 45
<211> LENGTH: 7
<212> TYPE: PRT
<213> ORGANISM: Artificial Sequence
<220> FEATURE:
<223> OTHER INFORMATION: Chemically synthesized

<400> SEQUENCE: 45

Phe Trp Phe Cys Gly Ala Lys
1               5

<210> SEQ ID NO 46
<211> LENGTH: 7
<212> TYPE: PRT
<213> ORGANISM: Artificial Sequence
<220> FEATURE:
<223> OTHER INFORMATION: Chemically synthesized

<400> SEQUENCE: 46

Phe Trp Phe Cys Gly Ala Ala
1               5

<210> SEQ ID NO 47
<211> LENGTH: 7
<212> TYPE: PRT
<213> ORGANISM: Artificial Sequence
<220> FEATURE:
<223> OTHER INFORMATION: Chemically synthesized

<400> SEQUENCE: 47

Asn Trp Ala Cys Cys Leu Asn
1               5

<210> SEQ ID NO 48
<211> LENGTH: 7
<212> TYPE: PRT
<213> ORGANISM: Artificial Sequence
<220> FEATURE:
<223> OTHER INFORMATION: Chemically synthesized

<400> SEQUENCE: 48

Asn Trp Leu Ala Cys Leu Asn
1               5

<210> SEQ ID NO 49
<211> LENGTH: 7
<212> TYPE: PRT
<213> ORGANISM: Artificial Sequence
<220> FEATURE:
<223> OTHER INFORMATION: Chemically synthesized

<400> SEQUENCE: 49

Ala Trp Ala Cys Cys Leu Asn
1               5

<210> SEQ ID NO 50
<211> LENGTH: 7
<212> TYPE: PRT
<213> ORGANISM: Artificial Sequence
<220> FEATURE:
<223> OTHER INFORMATION: Chemically synthesized

<400> SEQUENCE: 50

Ala Trp Leu Ala Cys Leu Asn
1               5

<210> SEQ ID NO 51
<211> LENGTH: 7
<212> TYPE: PRT
<213> ORGANISM: Artificial Sequence
<220> FEATURE:
<223> OTHER INFORMATION: Chemically synthesized

<400> SEQUENCE: 51

Ala Trp Leu Cys Cys Leu Ala
1               5

<210> SEQ ID NO 52
<211> LENGTH: 7
<212> TYPE: PRT
<213> ORGANISM: Artificial Sequence
<220> FEATURE:
<223> OTHER INFORMATION: Chemically synthesized

<400> SEQUENCE: 52

Asn Trp Ala Ala Cys Leu Asn
1               5

<210> SEQ ID NO 53
<211> LENGTH: 7
<212> TYPE: PRT
<213> ORGANISM: Artificial Sequence
<220> FEATURE:
<223> OTHER INFORMATION: Chemically synthesized

<400> SEQUENCE: 53

Asn Trp Ala Cys Cys Leu Ala
1               5

<210> SEQ ID NO 54
<211> LENGTH: 7
<212> TYPE: PRT
<213> ORGANISM: Artificial Sequence
<220> FEATURE:
<223> OTHER INFORMATION: Chemically synthesized

<400> SEQUENCE: 54

Asn Trp Leu Ala Cys Leu Ala
1               5

<210> SEQ ID NO 55
<211> LENGTH: 7
<212> TYPE: PRT
<213> ORGANISM: Artificial Sequence
<220> FEATURE:
<223> OTHER INFORMATION: Chemically synthesized

<400> SEQUENCE: 55

Ala Trp Ala Ala Cys Leu Asn
1               5

<210> SEQ ID NO 56
<211> LENGTH: 7
<212> TYPE: PRT
<213> ORGANISM: Artificial Sequence
<220> FEATURE:
<223> OTHER INFORMATION: Chemically synthesized

<400> SEQUENCE: 56

Ala Trp Ala Cys Cys Leu Ala
1               5

<210> SEQ ID NO 57
<211> LENGTH: 7
<212> TYPE: PRT
<213> ORGANISM: Artificial Sequence
<220> FEATURE:
<223> OTHER INFORMATION: Chemically synthesized

<400> SEQUENCE: 57

Ala Trp Leu Ala Cys Leu Ala
1               5

<210> SEQ ID NO 58
<211> LENGTH: 7
<212> TYPE: PRT
<213> ORGANISM: Artificial Sequence
<220> FEATURE:
<223> OTHER INFORMATION: Chemically synthesized

<400> SEQUENCE: 58

Asn Trp Ala Ala Cys Leu Ala
1               5

<210> SEQ ID NO 59
<211> LENGTH: 7
<212> TYPE: PRT
<213> ORGANISM: Artificial Sequence
<220> FEATURE:
<223> OTHER INFORMATION: Chemically synthesized

<400> SEQUENCE: 59

Ala Trp Ala Ala Cys Leu Ala
1               5

```
<210> SEQ ID NO 60
<211> LENGTH: 19
<212> TYPE: PRT
<213> ORGANISM: Artificial Sequence
<220> FEATURE:
<223> OTHER INFORMATION: Chemically synthesized

<400> SEQUENCE: 60

Phe Trp Phe Cys Gly Ala Lys Pro Gly Arg Lys Lys Arg Arg Gln Arg
1               5                   10                  15

Arg Arg Gly

<210> SEQ ID NO 61
<211> LENGTH: 19
<212> TYPE: PRT
<213> ORGANISM: Artificial Sequence
<220> FEATURE:
<223> OTHER INFORMATION: Chemically synthesized

<400> SEQUENCE: 61

Phe Trp Phe Cys Gly Leu Ala Pro Gly Arg Lys Lys Arg Arg Gln Arg
1               5                   10                  15

Arg Arg Gly

<210> SEQ ID NO 62
<211> LENGTH: 19
<212> TYPE: PRT
<213> ORGANISM: Artificial Sequence
<220> FEATURE:
<223> OTHER INFORMATION: Chemically synthesized

<400> SEQUENCE: 62

Phe Trp Phe Cys Gly Ala Ala Pro Gly Arg Lys Lys Arg Arg Gln Arg
1               5                   10                  15

Arg Arg Gly

<210> SEQ ID NO 63
<211> LENGTH: 19
<212> TYPE: PRT
<213> ORGANISM: Artificial Sequence
<220> FEATURE:
<223> OTHER INFORMATION: Chemically synthesized

<400> SEQUENCE: 63

Ala Trp Leu Cys Cys Leu Asn Pro Gly Arg Lys Lys Arg Arg Gln Arg
1               5                   10                  15

Arg Arg Gly

<210> SEQ ID NO 64
<211> LENGTH: 19
<212> TYPE: PRT
<213> ORGANISM: Artificial Sequence
<220> FEATURE:
<223> OTHER INFORMATION: Chemically synthesized

<400> SEQUENCE: 64

Asn Trp Ala Cys Cys Leu Asn Pro Gly Arg Lys Lys Arg Arg Gln Arg
1               5                   10                  15

Arg Arg Gly

<210> SEQ ID NO 65
<211> LENGTH: 19
<212> TYPE: PRT
<213> ORGANISM: Artificial Sequence
```

```
<220> FEATURE:
<223> OTHER INFORMATION: Chemically synthesized

<400> SEQUENCE: 65

Asn Trp Leu Ala Cys Leu Asn Pro Gly Arg Lys Lys Arg Arg Gln Arg
1               5                   10                  15

Arg Arg Gly

<210> SEQ ID NO 66
<211> LENGTH: 19
<212> TYPE: PRT
<213> ORGANISM: Artificial Sequence
<220> FEATURE:
<223> OTHER INFORMATION: Chemically synthesized

<400> SEQUENCE: 66

Asn Trp Leu Cys Cys Leu Ala Pro Gly Arg Lys Lys Arg Arg Gln Arg
1               5                   10                  15

Arg Arg Gly

<210> SEQ ID NO 67
<211> LENGTH: 19
<212> TYPE: PRT
<213> ORGANISM: Artificial Sequence
<220> FEATURE:
<223> OTHER INFORMATION: Chemically synthesized

<400> SEQUENCE: 67

Ala Trp Ala Cys Cys Leu Asn Pro Gly Arg Lys Lys Arg Arg Gln Arg
1               5                   10                  15

Arg Arg Gly

<210> SEQ ID NO 68
<211> LENGTH: 19
<212> TYPE: PRT
<213> ORGANISM: Artificial Sequence
<220> FEATURE:
<223> OTHER INFORMATION: Chemically synthesized

<400> SEQUENCE: 68

Ala Trp Leu Ala Cys Leu Asn Pro Gly Arg Lys Lys Arg Arg Gln Arg
1               5                   10                  15

Arg Arg Gly

<210> SEQ ID NO 69
<211> LENGTH: 19
<212> TYPE: PRT
<213> ORGANISM: Artificial Sequence
<220> FEATURE:
<223> OTHER INFORMATION: Chemically synthesized

<400> SEQUENCE: 69

Ala Trp Leu Cys Cys Leu Ala Pro Gly Arg Lys Lys Arg Arg Gln Arg
1               5                   10                  15

Arg Arg Gly

<210> SEQ ID NO 70
<211> LENGTH: 19
<212> TYPE: PRT
<213> ORGANISM: Artificial Sequence
<220> FEATURE:
<223> OTHER INFORMATION: Chemically synthesized
```

<400> SEQUENCE: 70

Asn Trp Ala Ala Cys Leu Asn Pro Gly Arg Lys Lys Arg Arg Gln Arg
1               5                   10                  15

Arg Arg Gly

<210> SEQ ID NO 71
<211> LENGTH: 19
<212> TYPE: PRT
<213> ORGANISM: Artificial Sequence
<220> FEATURE:
<223> OTHER INFORMATION: Chemically synthesized

<400> SEQUENCE: 71

Asn Trp Ala Cys Cys Leu Ala Pro Gly Arg Lys Lys Arg Arg Gln Arg
1               5                   10                  15

Arg Arg Gly

<210> SEQ ID NO 72
<211> LENGTH: 19
<212> TYPE: PRT
<213> ORGANISM: Artificial Sequence
<220> FEATURE:
<223> OTHER INFORMATION: Chemically synthesized

<400> SEQUENCE: 72

Asn Trp Leu Ala Cys Leu Ala Pro Gly Arg Lys Lys Arg Arg Gln Arg
1               5                   10                  15

Arg Arg Gly

<210> SEQ ID NO 73
<211> LENGTH: 19
<212> TYPE: PRT
<213> ORGANISM: Artificial Sequence
<220> FEATURE:
<223> OTHER INFORMATION: Chemically synthesized

<400> SEQUENCE: 73

Ala Trp Ala Ala Cys Leu Asn Pro Gly Arg Lys Lys Arg Arg Gln Arg
1               5                   10                  15

Arg Arg Gly

<210> SEQ ID NO 74
<211> LENGTH: 19
<212> TYPE: PRT
<213> ORGANISM: Artificial Sequence
<220> FEATURE:
<223> OTHER INFORMATION: Chemically synthesized

<400> SEQUENCE: 74

Ala Trp Ala Cys Cys Leu Ala Pro Gly Arg Lys Lys Arg Arg Gln Arg
1               5                   10                  15

Arg Arg Gly

<210> SEQ ID NO 75
<211> LENGTH: 19
<212> TYPE: PRT
<213> ORGANISM: Artificial Sequence
<220> FEATURE:
<223> OTHER INFORMATION: Chemically synthesized

```
<400> SEQUENCE: 75

Ala Trp Leu Ala Cys Leu Ala Pro Gly Arg Lys Lys Arg Arg Gln Arg
1               5                   10                  15

Arg Arg Gly

<210> SEQ ID NO 76
<211> LENGTH: 19
<212> TYPE: PRT
<213> ORGANISM: Artificial Sequence
<220> FEATURE:
<223> OTHER INFORMATION: Chemically synthesized

<400> SEQUENCE: 76

Asn Trp Ala Ala Cys Leu Ala Pro Gly Arg Lys Lys Arg Arg Gln Arg
1               5                   10                  15

Arg Arg Gly

<210> SEQ ID NO 77
<211> LENGTH: 19
<212> TYPE: PRT
<213> ORGANISM: Artificial Sequence
<220> FEATURE:
<223> OTHER INFORMATION: Chemically synthesized

<400> SEQUENCE: 77

Ala Trp Ala Ala Cys Leu Ala Pro Gly Arg Lys Lys Arg Arg Gln Arg
1               5                   10                  15

Arg Arg Gly

<210> SEQ ID NO 78
<211> LENGTH: 120
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (103)..(109)
<223> OTHER INFORMATION: Amino acids at positions 103, 104, 105, 106,
      107, 108 and 109 are Xaa wherein Xaa: any amino acid.

<400> SEQUENCE: 78

Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45

Glu Ser Tyr Cys Gln Arg Gln Gly Val Pro Met Asn Ser Leu Arg Phe
    50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr Ala
                85                  90                  95

Arg Gly Gly Gly Gly Ser Xaa Xaa Xaa Xaa Xaa Xaa Xaa Pro Gly Lys
            100                 105                 110

Lys Arg Arg Gln Arg Arg Gly
            115                 120
```

-continued

```
<210> SEQ ID NO 79
<211> LENGTH: 102
<212> TYPE: PRT
<213> ORGANISM: Artificial Sequence
<220> FEATURE:
<223> OTHER INFORMATION: Chemically synthesized

<400> SEQUENCE: 79

Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45

Glu Ser Tyr Cys Gln Arg Gln Gly Val Pro Met Asn Ser Leu Arg Phe
    50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr Ala
                85                  90                  95

Arg Gly Gly Gly Gly Ser
            100

<210> SEQ ID NO 80
<211> LENGTH: 10
<212> TYPE: PRT
<213> ORGANISM: Artificial Sequence
<220> FEATURE:
<223> OTHER INFORMATION: Chemically synthesized

<400> SEQUENCE: 80

Pro Pro Asn Pro Lys Lys Glu Ile Glu Leu
1               5                   10
```

INTERACTING POLYPEPTIDE COMPRISING A HEPTAPEPTIDE PATTERN AND A CELLULAR PENETRATION DOMAIN

This application is a continuation of PCT International Application No. PCT/FR2004/002479, filed Sep. 30, 2004, which claims priority of French Patent Application No. 0311463, filed Sep. 30, 2003, the contents of all of which are hereby incorporated by reference into this application.

The present invention relates to interacting polypeptides comprising a heptapeptide motif (pattern) and a cell penetration region, and to screening methods for identifying interacting polypeptides capable of modifying the phenotype of a cell and for identifying other molecules capable of interacting with an intracellular target. The present invention also relates to the use of interacting polypeptides as mentioned above in phenotype screens or for therapeutic purposes. Finally, the present invention is directed towards particular interacting polypeptides capable of modifying the function of the Rev viral protein and their use in screening methods for the identification of other molecules capable of interacting with Rev.

Peptide interactions are primarily responsible for intra- and inter-cellular communication; the cell functions and adapts to its environment via a complex set of interactions between a protein and its ligand. When novel proteins are identified, this knowledge may at first appear to be of no interest until the partners for that novel protein can be identified, whereupon the cellular function of the protein can be determined.

Further, in the majority of cases, a protein is capable of interacting with different partners. From these interactions, the same function may arise as regards each of the partners (for example a protein phosphorylating different peptide ligands), or completely distinct functions may arise therefrom. This is particularly the case with membrane proteins which, independently of their natural function in the cell, also act as a point of entry for viruses. The function of any given protein is thus primarily determined by the peptides or proteins with which that protein interacts.

Protein interactions are in general a combination of local interactions between highly specific sites on the protein (a few amino acids) by dint of various bonds such as electrostatic bonds, hydrogen bonds and repulsive interactions due to steric hindrance.

A given protein may interact specifically with a protein domain, with the result that protein may interact with a whole class of protein which shares that domain.

While for a given protein, in general only a small number of natural peptide partners are known, its interaction capacity is much more important. A given protein may have numerous sites which are capable of generating interactions and which are accessible to other peptides.

Thus, determining novel interacting partners may allow either to modify (perturb, prevent, improve, change the kinetics, specificity, etc) interactions, or allow existing interactions to be mimicked, or bring novel interactions to light.

The identification of novel interacting partners is generally carried out under two different situations.

In a first case, a partner is sought for a predetermined target, which may be intracellular or extracellular. In such a case, it is possible to produce a particular polypeptide which may interact with the target. The sequence of that polypeptide is determined by taking into account the structure of the target protein with which it has to interact, the charge distribution, attractive and repulsive forces. That step is usually carried out by molecular modeling. That approach necessitates very detailed knowledge of the target protein, in particular its three-dimensional structure. It is also possible to screen to test many potential polypeptides against the target. The screen must be able to demonstrate an interaction between one of the test polypeptides and the predetermined target. A screen which is generally used in such a case is the yeast two-hybrid screening system (U.S. Pat. No. 5,580,736) where the predetermined target and the potential polypeptide are expressed simultaneously.

In a second case, the target protein is not determined, i.e. novel interacting partners may also be screened for their capacity to modify a given phenotype of the cell, without knowing the target protein with which they interact. In that case, phenotype screens are used which consist of expressing different polypeptides via the cell and identifying those which are capable of modifying the phenotype in the expected direction (U.S. Pat. No. 6,153,380).

A variation of that situation consists of screening novel interacting partners which are capable of preventing, destroying, modifying or destabilizing an interaction between two other proteins. In that case too, phenotype screens are generally used. The mode via which the partner acts on the interaction between the other two proteins is not necessarily known.

To produce polypeptides to be used in the screens mentioned above, numerous constructs have been proposed, characterized in particular by the simultaneous presence of a fixed protein sequence (sometimes termed a platform) within which is inserted a motif the sequence of which is random (see International patent application WO-A-96/02561). By varying that sequence, it is then possible to produce a whole family of polypeptides and to test them in succession for their capacity to interact within the cell.

When that approach is used to determine novel interacting partners for intracellular proteins, it generally resorts to cloning and transformations which allow the construct to be tested to be expressed in the cell in which the protein for which a novel interacting partner is sought is expressed.

In the therapeutic field this means that, if a potential partner is detected, a drug must then be able to be made from it which will act inside the cell, i.e. a means must be found to cause it to penetrate into the cell. Gene therapy normally cannot accomplish that step easily. The other solution, consisting of grafting a motif which encourages cell penetration onto the interacting partner, suffers from the disadvantage of modifying the interacting partner in a manner which cannot be predicted. After this modification, it is not guaranteed that it will still be capable of interacting with the protein which has been selected as a ligand.

A further approach consists of producing protein mimics by modeling, but that method is still not fully developed. Further, molecules are often produced which are not capable, or cannot readily, traverse the membrane of the cell, and which thus do not bring about the interaction for which they have been produced. If a motif which guarantees cell penetration has to be grafted onto these molecules, as in the case above, it is not guaranteed that they would still be capable of interacting with the protein for which they have been selected as a ligand.

The aim of the present invention is to propose novel interacting peptides having a particular construction such that a cell penetration domain is associated with the interacting partner. If such a partner is shown, after a first screening, to be capable of interacting with the partner of interest, passage from screening to generation of a drug does not add a new motif which could risk perturbing the interaction demonstrated during the screening step.

The interacting peptides of the invention have the dual property of cell penetration, for example into lymphocytes and/or macrophages, and interaction with a partner.

The inventors have developed a method which can produce small proteins having a heptapeptide motif and are capable of binding to a protein target of viral or cellular origin, thereby inhibiting its activity. These small proteins have been designed to be able to penetrate into cells.

The interacting polypeptide of the invention may also have a stabilization domain, linkers or other components.

The present invention also proposes different screening methods for producing novel polypeptides which are capable of modifying a given phenotype or of interacting with a given target. The present invention also proposes a method for screening chemical molecules which are capable of interacting with a given protein target.

A domain in which the determination of such partners is important is virus replication. Replication of certain viruses in human or animal cells is permitted by the expression of a limited number of viral proteins, certain of which have an essential activity in bringing about this process. By blocking those proteins by an interacting polypeptide defined in accordance with the screens of the present invention, which is thus capable of penetrating into cells and preventing the necessary contact with other viral or cellular proteins, it is possible to prevent virus replication.

In implementing the invention, it has been possible to identify partners capable of interacting with the Rev protein, in particular the Rev protein of HIV-1 and thus to prevent virus replication. These polypeptides also form part of the present invention.

The invention may also be implemented in methods aimed at identifying partners capable of interacting with various proteins involved in certain cancers.

Within the context of the present invention, the terms below are defined as follows:

Heptapeptide or heptapeptide motif: linear concatenation of 7 covalently bonded consecutive amino acids;

(Peptide) domain: peptide sequence comprising at least 5 amino acids which, in a sequence comprising it, may be defined by deletion-mutation analysis. Such a domain is generally responsible for a function or a role and is characterized by the presence of essential amino acids the mutation of which causes a loss of function. Examples which may be cited are the NLS (nuclear localization signal) domain present in many proteins of the nucleus, the cell penetration domain, the NES (nuclear export signal) domain, protein-protein interaction domains, and catalytic domains.

Cell penetration or transduction domain or motif: peptide sequence comprising 5 to 35 amino acids capable of causing in vivo, ex vivo or in vitro penetration into the cell of a protein containing that domain.

To ensure cell penetration, the domain may have to be placed at one end of the protein, for example at the C-terminal end; the cell penetration function may also be indifferent to the position of the motif in the protein. The cell penetration function is possibly limited to a certain protein size beyond which penetration is no longer assured.

The cell penetration motif is either general to all cell types or specific to certain membranes, for example to the membranes of prokaryotic cells or to membranes of Gram+ bacteria or Gram− bacteria, or to membranes of certain human cell types such as lymphocytes, for example primary lymphocytes, and/or macrophages.

The penetration motif may also ensure penetration into the nucleus of eukaryotic cells.

Stabilization domain or motif: sequence of amino acids comprising at least 30 amino acids the secondary structure of which is stable over time and under certain stress conditions, and which has the capacity to stabilize any chimeric protein which comprises it. In particular, the structure must be insensitive to denaturing and to degradation by proteases and stress conditions in general; this structure must be only slightly perturbed in the case of insertion into or at the ends of that domain. The stabilization domain is also characterized by a low immunogenic nature. Preferably, a stabilization domain is relatively modest in size, and thus has les than 300 amino acids, preferably less than 200 amino acids.

In general, in most cases, a stabilization domain is a fragment of a natural protein present in the cell, which protein must be selected from proteins in the cell which are abundant, ubiquitous and not involved in degradation processes.

Random sequence: a sequence which is defined or constructed by a random process.

In the case of a DNA sequence, the random sequence consists of selecting deoxyribonucleotides one by one from four possibles, each having (equiprobable) or not having (biased choice) the same probability of being selected. Because of the degeneracy of the genetic code, a random DNA sequence with equiprobability of 4 bases will produce a random peptide sequence but with a bias as amino acids coded by several codons will be over represented compared with others.

The probability that a random DNA sequence of 21 bases (i.e. 7 amino acids) does not contain the stop codon in phase is 71.5%.

It may also be a peptide sequence which is defined in a random manner, i.e. the amino acids are determined in succession by selection from all possible amino acids, with or without equiprobability.

Bait: in a screening with the aim of determining novel molecules which are capable of interacting together, the bait is the pre-defined, predetermined molecule for which a ligand is sought by means of the screening.

The bait may or may not be fused to a molecule acting as a reporter.

Prey: in this same screening, the prey is the molecule which is tested for its capacity to interact with a predetermined bait.

The prey may or may not be fused to a molecule acting as a reporter.

Two-hybrid system: this is a particular screening which was initially developed in yeast but the principle of which may be adapted to other cell types.

In two-hybrid target, the DNA sequence coding for the bait is fused in phase to a "d1" sequence coding for a first domain, "D1". The sequence coding for the prey is fused in phase to a sequence "d2" coding for a second domain "D2". The domains "D1" and "D2" are characterized in that their combination "D1+D2" has a particular property or function which the elements "D1" and "D2" do not have separately. The combination of "D1" and "D2" necessitates an external intervention to place and maintain them in contact. After translation, the possible interaction of the bait (fused to "D1") and the prey (fused to "D2") will cause combination of "D1" and "D2". The particular property or function which results from this combination "D1+D2" enables the interaction between the bait and the prey to be demonstrated.

Chimeric polypeptide: polypeptide comprising a covalent fusion of at least two amino acid sequences which are not naturally contiguous in the same protein. Covalent fusion may be accomplished by a direct or indirect (via a linker) covalent bond.

It may concern two sequences derived from two proteins of the same cell, or from two proteins deriving from cells of a close or distant genus, for example different animal species, or a sequence of a eukaryotic cell protein and the other from a prokaryotic cell. It may also concern the covalent fusion of a sequence of a protein with a synthetic sequence which is not naturally present in said protein.

Linker: very short amino acid sequence, generally comprising 1 to 10 amino acids, preferably 1 to 5, present between two domains of a polypeptide which it separates. Linkers are selected so that they do not interfere functionally with the two domains they separate. The use of linkers is also particularly recommended to allow each domain to adopt a three dimensional folding independently of each other.

Linkers are generally rich in glycine amino acids as they have very little steric hindrance on the side chain and are of low reactivity. Prolines are also very often inserted into linkers because of their properties which favor the formation of bends and thus the two domains which the linker separates have greater independence.

Percentage identity between two protein sequences: this percentage indicates the degree of identity between two amino acid sequences along the whole sequence. If the sequences under consideration have different sizes, the % identity is expressed as a function of the total length of the longest sequence. To calculate the % identity, the two sequences are superimposed to maximize the number of identical amino acids, using gaps of finite length, then the number of identical amino acids is divided by the total number of amino acids in the longest sequence. This definition is that used in the present invention.

In a first aspect, the invention concerns an interacting polypeptide comprising a heptapeptide motif with the sequence $^N X_1 X_2 X_3 X_4 X_5 X_6 X_7^C$ and a cell penetration domain, in which $X_1$, $X_2$, $X_3$, $X_4$, $X_5$, $X_6$ and $X_7$ are amino acids. The interacting polypeptide of the invention is a chimeric polypeptide; its "chimeric" nature derives from the fusion of the heptapeptide motif and the cell penetration domain, i.e. this concatenation is not naturally present in any protein.

Further, a polypeptide of the invention is characterized by a particular disposition of the heptapeptide motif with respect to the cell penetration domain. In fact, the amino acid $X_7$ is found 5 to 35 amino acids from the C-terminal end of said polypeptide, preferably 7 to 25, more preferably 9 to 20, for example 12 to 15, and the cell penetration domain is located at the C-terminal end with respect to the heptapeptide motif. The transduction domain may be placed at the C-terminal end of the interacting polypeptide; it may also be disposed at the C-terminal end with respect to the heptapeptide motif, without being at the C-terminal end; for example, it might be followed by a His tag or another motif which allows the interacting polypeptide to be purified or detected.

The heptapeptide motif present in the interacting polypeptide of the invention is a concatenation of 7 amino acids. Preferably, the amino acids are selected from the 20 naturally existing amino acids. However, in the context of the invention, modified amino acids may also be incorporated.

As an example, the heptapeptide motif is generated by a random process. It may also be coded by a DNA sequence which has itself been generated by a random process. In contrast, the heptapeptide motif may be entirely selected and predetermined, optionally after a molecular modeling step when the interacting polypeptide is screened for its capacity to interact with a predetermined protein.

The length of 7 amino acids for the motif is particularly advantageous, in particular when the motif is coded by a DNA sequence generated by a random process. When the DNA sequence is generated in a random manner, this may result in the production of stop codons (TAA, TAG and TGA). A length of 7 amino acids, i.e. 21 nucleotides, produces relatively few stop codons and useless sequences while remaining sufficiently long for a domain which is capable of interaction to be produced. The number 7 for the length of the heptapeptide motif thus appears to be an advantageous compromise.

A further advantage of the number 7 lies in the fact that a sequence of this length has little probability of being immunogenic. It is known that the antigens presented by the major histocompatiblity complex class I (MHC class I) have a minimum length of 8 or 9 amino acids, i.e. longer than the heptapeptide length.

An interacting polypeptide of the present invention thus comprises at least 12 to 42 amino acids. It is generally admitted that polypeptides of this size may sometimes be unstable in the cell and they are favored targets for proteases with the exception, however, of a few peptides such as antimicrobial peptides. For this reason, an interacting polypeptide of the present invention is preferably coupled to a molecule which will stabilize the assembly. Preferably, such stabilization is achieved by integrating a stabilization domain with the interacting polypeptide sequence.

The stabilization domain is characterized by stability over time of the polypeptide comprising it which is greater than that of the same polypeptide without a stabilization domain. It is also characterized by its stability under stress conditions, for example denaturing and cleavage conditions which may occur in vitro or in vivo. A given stabilization domain may also be selected for its stability in certain particular biological media such as the intestinal medium or the seric medium, for example, so that the interacting partners containing such a domain would be stable in the event of ingestion or passage into the blood stream. Independently of its stabilizing role, a stabilization domain may also have characteristics allowing it to be detected.

A further advantage of the stabilization domain is its capacity to be produced in bacteria or in another organism which can produce recombinant proteins, in large quantities and in a stable form.

Preferred stabilization domains include fragments of natural proteins. Certain proteins are particularly abundant in the cell, ubiquitous, non immunogenic and stable. Fragments of such proteins are thus particularly preferred for use as a stabilization domain. This is particularly the case with proteins from the ubiquitin family (ubiquitin-like).

When the interacting polypeptide is to be introduced into a given cell, it has been shown to be particularly advantageous to select, as the stabilization domain, a fragment of a protein present in said cell or a protein belonging to the species of which the cell forms a part. In the context of the present invention, it is thus advantageous to select the stabilization domain from fragments of proteins present in human or in animal cells.

The inventors have demonstrated that one member of the ubiquitin family, truncated in its C-terminal portion to remove the diglycine motif and all sequences downstream of that motif, has very advantageous properties as regards a stabilization domain.

A particularly preferred protein in the context of the present invention is the ubiquitin homologue known as SUMO-1. A fragment of SUMO-1 which is particularly suitable as regards the present invention is the fragment illustrated in FIG. 6 (SEQ ID NO: 1) where the diglycine motif and all sequences downstream thereof have been truncated.

For use as a stabilization domain in the context of the present invention, any sequence having at least 80% identity, preferably at least 90% or at least 95% identity with the sequence mentioned above is particularly advantageous.

Other proteins or protein fragments may also be adapted to this "stabilization domain" function, in particular chaperone proteins such as heat shock proteins (HSP).

One alternative to the use of a stabilization domain consists in cyclizing the interacting partners, to obtain the same stabilization effect. The term "cyclization" means peptide fusion of the N-terminal portion upstream of the heptapeptide domain with the C-terminal end of the interacting polypeptide.

According to the present invention, it is envisaged that very short amino acid sequences termed linkers should be present either between the stabilization domain if there is one and the heptapeptide motif, or between the heptapeptide motif and the transduction domain. These linkers are principally intended to link the various domains of the polypeptide.

This role is thus, for example, to isolate the domains so that there is no interaction between the domains, for example simply by separating them by a sufficient number of amino acids interacting neither with one domain nor with the other domain. The two domains may then fold in a manner which is not influenced by the presence of the other domain.

The role of the linker may also be to impose a particular positioning from one domain to another, in particular by forming a bend, which also generally has the result of isolating one domain from the other.

Finally, the domain may also comprise amino acids which are known as sites for cleavage by certain proteases, preferably intracellular. This approach may, after cell penetration, allow separation of the two domains by cleaving at the linker site.

Conversely, a linker may be selected so that it is particularly resistant to proteases, to avoid potential cleavage, for example, of the cell penetration domain before the penetration step.

Preferably, a linker of the invention comprises mainly low reactivity, low hindrance amino acids, i.e. amino acids with a side chain which only contains a few atoms, which is particularly the case with the amino acids glycine and proline. Further, proline generally forms a bend in the chain into which it is inserted, this property being exploited to isolate one domain from another.

Preferably, a linker of the present invention comprises 5 or fewer amino acids.

A linker of the invention can introduce a degree of flexibility between the various functional portions of the protein.

A linker which is particularly suitable for the present invention comprises less than 5 amino acids and at least about 20% of the amino acids glycine and proline, preferably at least 50%. In a particular situation, a linker of the present invention comprises only amino acids selected from glycine and proline. As an example, a linker of the invention may have the sequence GGGG or PG, G signifying glycine and P signifying proline, and the sequences are written conventionally from the N-terminal end to the C-terminal end.

An interacting polypeptide of the invention comprises a cell penetration domain of 5 to 35 amino acids which is found in its C-terminal end; this cell penetration domain allows penetration of the polypeptide into the cell.

Various domains identified in the literature may be used for this purpose. Particularly preferred domains for use in the context of the present invention are found in the penetration domain of the HIV-Tat protein, or domains from other viral strains having the same activity.

The cell penetration domain in the HIV-Tat protein is characterized by the following sequence: $^N$RKKRRQRRR$^C$ (SEQ ID NO: 9), in which the one-letter code has been used to represent the amino acids. The present invention also envisages the use of a cell penetration domain essentially corresponding to the preceding sequence where several amino acids have been mutated, in particular to improve the penetration properties, to increase the resistance to proteases or to reduce a possible immune response.

The intracellular penetration domain of the interacting polypeptide of the invention may also comprise a polyarginine motif with sequence RRRRRRR (SEQ ID NO: 22), RRRRRRRR (SEQ ID NO: 23) or RRRRRRRRR (SEQ ID NO: 24) (7 to 9 amino acids—arginine) the penetration role of which has been demonstrated in lymphocytes (Wender et al, 2000).

A further transduction domain also envisaged in the present invention has a sequence partially corresponding to that of the transduction domain of Tat but incorporating some modifications: RRKARRQRRR (SEQ ID NO: 21).

A particular construction for an interacting polypeptide of the invention consists of placing the amino acid $X_7$ of the heptapeptide motif between 10 and 30 amino acids from the C-terminal end of the polypeptide, preferably between 12 and 28, more preferably between 15 and 25 amino acids from the C-terminal end.

Regarding the choice of stabilization domain for an interacting polypeptide of the present invention, a particularly suitable domain is the SUMO-1 protein. Preferably, the stabilization domain used is the fragment of the SUMO-1 protein the sequence of which is shown in FIG. 6 (SEQ ID NO: 1), or any domain sharing at least 80% identity, preferably 90% identity with that sequence.

A further domain which may be used in the context of the invention is the ubiquitin fragment defined by the sequence shown in FIG. 6.

Other domains or elements advantageously form part of an interacting polypeptide or are grafted to said polypeptide. In particular, it is of particular advantage to incorporate an addressing sequence into the sequence of the polypeptide, or a sequence facilitating its detection and monitoring, for example its localization or degradation. Examples of sequences facilitating detection which may be envisaged are sequences having a readily detectable enzymatic property, or a reactivity with a predetermined antibody, or fluorescent properties. Grafting or incorporating into the sequence of a polypeptide a sequence facilitating its purification, for example by providing a polyhistidine tail or His-Tag, may also be envisaged.

Addressing signals which can preferentially deliver the polypeptide of the invention to certain types of cells are also particularly advantageous in the present invention. Particularly attractive target cells are lymphocytes, macrophages, Langerhans cells, dendritic cells, stem cells, muscle cells, etc. Such addressing signals may form part of the stabilization domain; they may also form part of a polypeptide of the invention above and beyond the stabilization domain, linkers, heptapeptide and the penetration domain. Alternatively, cell penetration domains may be used which are specific or preferential to certain cell types.

Particularly preferred sequences for the heptapeptide motif which may be cited are sequences having at least one of the following characteristics: $X_2$ is the amino acid tryptophan, $X_4$ and/or $X_5$ is the amino acid cysteine. Other sequences of the invention are also leucine for the amino acid $X_5$. Preferably, the sequence of the heptapeptide motif comprises tryptophan at $X_2$ and cysteine at $X_4$ and/or $X_5$. A heptapeptide motif preferably comprises the 3 characteristics mentioned above.

Particularly preferred heptapeptide sequences in the context of the present invention are those interacting with the Rev protein of HIV-1, as follows:

| | |
|---|---|
| $^N$FWFCGLK$^C$, | (SEQ ID NO: 2) |
| $^N$NWLCCLN$^C$, | (SEQ ID NO: 3) |
| $^N$KLGCFWF$^C$, | (SEQ ID NO: 10) |
| $^N$NLCCLWN$^C$, | (SEQ ID NO: 11) |
| $^N$FWFCGLA$^C$, | (SEQ ID NO: 27) |
| $^N$AWLCCLN$^C$, | (SEQ ID NO: 25) |
| $^N$NWLCCLA$^C$, | (SEQ ID NO: 26) |
| FWFCGAK, | (SEQ ID NO: 45) |
| FWFCGAA, | (SEQ ID NO: 46) |
| NWACCLN, | (SEQ ID NO: 47) |
| NWLACLN, | (SEQ ID NO: 48) |
| AWACCLN, | (SEQ ID NO: 49) |
| AWLACLN, | (SEQ ID NO: 50) |
| AWLCCLA, | (SEQ ID NO: 51) |
| NWAACLN, | (SEQ ID NO: 52) |
| NWACCLA, | (SEQ ID NO: 53) |
| NWLACLA, | (SEQ ID NO: 54) |
| AWAACLN, | (SEQ ID NO: 55) |
| AWACCLA, | (SEQ ID NO: 56) |
| AWLACLA, | (SEQ ID NO: 57) |
| NWAACLA and | (SEQ ID NO: 58) |
| AWAACLA. | (SEQ ID NO: 59) |

Sequences of 7 amino acids obtained from the above sequences by substituting a single amino acid are also preferred.

Particularly preferred sequences for an interacting polypeptide of the invention which may be cited are the following:

| | |
|---|---|
| FWFCGLKPGRKKRRQRRRG, | (SEQ ID NO: 4) |
| NWLCCLNPGRKKRRQRRRG, | (SEQ ID NO: 5) |
| FWFCGAKPGRKKRRQRRRG, | (SEQ ID NO: 60) |
| FWFCGLAPGRKKRRQRRRG, | (SEQ ID NO: 61) |
| FWFCGAAPGRKKRRQRRRG, | (SEQ ID NO: 62) |
| AWLCCLNPGRKKRRQRRRG, | (SEQ ID NO: 63) |
| NWACCLNPGRKKRRQRRRG, | (SEQ ID NO: 64) |
| NWLACLNPGRKKRRQRRRG, | (SEQ ID NO: 65) |
| NWLCCLAPGRKKRRQRRRG, | (SEQ ID NO: 66) |
| AWACCLNPGRKKRRQRRRG, | (SEQ ID NO: 67) |
| AWLACLNPGRKKRRQRRRG, | (SEQ ID NO: 68) |
| AWLCCLAPGRKKRRQRRRG, | (SEQ ID NO: 69) |
| NWAACLNPGRKKRRQRRRG, | (SEQ ID NO: 70) |
| NWACCLAPGRKKRRQRRRG, | (SEQ ID NO: 71) |
| NWLACLAPGRKKRRQRRRG, | (SEQ ID NO: 72) |
| AWAACLNPGRKKRRQRRRG, | (SEQ ID NO: 73) |
| AWACCLAPGRKKRRQRRRG, | (SEQ ID NO: 74) |
| AWLACLAPGRKKRRQRRRG, | (SEQ ID NO: 75) |
| NWAACLAPGRKKRRQRRRG | (SEQ ID NO: 76) |
| et AWAACLAPGRKKRRQRRRG. | (SEQ ID NO: 77) |

A polypeptide of the invention thus has the capacity to penetrate inside a cell without external intervention when it is brought into contact with the cell. It also has the capacity to interact with a protein or a protein domain which may be intracellular or extracellular.

Further, the structure of the polypeptide itself ensures great flexibility, in particular as regards the variable portion which is the heptapeptide motif. This motif is in fact placed less than 35 amino acids from the C-terminal portion of the polypeptide, preferably less than 25 amino acids. This advantageous position in a part of the polypeptide which suffers fewer conformational stresses than in the more central portion of the polypeptide, ensures that the heptapeptide has greater folding freedom. This increased freedom highly probably results in an increased capacity to adapt to its target. When the stresses are low at each end of the heptapeptide, it may adopt a larger number of conformations as the energy barrier to pass from one conformation to another is lower. This flexibility results in different possible conformations for a given heptapeptide and thus a greater probability of interaction with the target.

In a further aspect, the present invention more particularly concerns peptides which are capable of interacting with the Rev protein, to inhibit replication thereof, characterized in that they consist of or comprise the heptapeptide sequence $^NX_1WX_3X_4X_5X_6X_7^C$ where $X_1$, $X_3$, $X_4$, $X_5$, $X_6$, and $X_7$ are amino acids selected independently from natural or modified amino acids and $X_4$ and/or $X_5$ is a cysteine, W is tryptophan. Preferably, $X_5$ is a cysteine.

The Rev protein is that of a viral HIV type strain, for example HIV-1 or HIV-2, or of the SIV type (simian immunodeficiency virus), SHIV (hybrid between the human and simian immunodeficiency virus), FIV (feline immunodeficiency virus) or any other viral strain having a protein homologous with the Rev protein of HIV-1; it may also be the equivalent Rex protein of HTLV1, HTLV2 or BLV.

Such peptides comprise or consist of a sequence which is capable of interacting with the Rev protein in a yeast two-hybrid system; further, these peptides are also capable of inhibiting viral replication in vivo. Preferred heptapeptide sequences are as follows:

| | |
|---|---|
| $^N$FWFCGLK$^C$, | (SEQ ID NO: 2) |
| $^N$NWLCCLN$^C$, | (SEQ ID NO: 3) |
| $^N$FWFCGLA$^C$, | (SEQ ID NO: 27) |
| $^N$AWLCCLN$^C$, | (SEQ ID NO: 25) |

-continued

| $^N$NWLCCLA$^C$, | (SEQ ID NO: 26) |
| FWFCGAK, | (SEQ ID NO: 45) |
| FWFCGAA, | (SEQ ID NO: 46) |
| NWACCLN, | (SEQ ID NO: 47) |
| NWLACLN, | (SEQ ID NO: 48) |
| AWACCLN, | (SEQ ID NO: 49) |
| AWLACLN, | (SEQ ID NO: 50) |
| AWLCCLA, | (SEQ ID NO: 51) |
| NWAACLN, | (SEQ ID NO: 52) |
| NWACCLA, | (SEQ ID NO: 53) |
| NWLACLA, | (SEQ ID NO: 54) |
| AWAACLN, | (SEQ ID NO: 55) |
| AWACCLA, | (SEQ ID NO: 56) |
| AWLACLA, | (SEQ ID NO: 57) |
| NWAACLA and | (SEQ ID NO: 58) |
| AWAACLA. | (SEQ ID NO: 59) |

In order to test the capacity of a peptide to interact with the Rev protein of HIV-1 in a yeast two-hybrid test, the following test, developed further in the experimental section, may be carried out:

Bait: plasmid pLexRev (see Example 1);
Prey: plasmid containing the activation domain of GAL4 in fusion with the sequence coding for the test peptide, for example a plasmid derived from pGAD424.
Yeast: HF7c strain of S. cerevisiae.

Example 1 provides more information regarding the operating conditions which may be envisaged for this test.

To test the capacity of the peptide to inhibit viral replication in vivo, the following test, developed further in the experimental section, may be carried out:

Cells: human cells, peripheral blood mononuclear;
Virus: lymphotropic strain with reference HIV-1-LAI (Barré-Sinoussi et al; 1983);
Protocol: the cells are pre-treated for 30 minutes in 5 concentrations of test peptide then infected with the HIV-1-LAI strain. The peptide is maintained in the medium throughout culture; the cellular supernatant is collected 7 days post infection and the reverse transcription activity is measured. The experimental section provides more information regarding the operating conditions, the concentrations and buffers which could be used to carry out this test.

The polypeptides comprising the sequences $^N$FWFCGLK-PGRKKRRQRRRG $^C$ (SEQ ID NO: 4), $^N$ NWLCCLN-PGRKKRRQRRRG $^C$ (SEQ ID NO: 5), FWFCGAK-PGRKKRRQRRRG (SEQ ID NO: 60), FWFCGLAPGRKKRRQRRRG (SEQ ID NO: 61), FWFC-GAAPGRKKRRQRRRG (SEQ ID NO: 62), AWLCCLN-PGRKKRRQRRRG (SEQ ID NO: 63), NWACCLN-PGRKKRRQRRRG (SEQ ID NO: 64), NWLACLNPGRKKRRQRRRG (SEQ ID NO: 65), NWL-CCLAPGRKKRRQRRRG (SEQ ID NO: 66), AWACCLN-PGRKKRRQRRRG (SEQ ID NO: 67), AWLACLN-PGRKKRRQRRRG (SEQ ID NO: 68), AWLCCLAPGRKKRRQRRRG (SEQ ID NO: 69), NWAA-CLNPGRKKRRQRRRG (SEQ ID NO: 70), NWAC-CLAPGRKKRRQRRRG (SEQ ID NO: 71), NWLA-CLAPGRKKRRQRRRG (SEQ ID NO: 72), AWAACLNPGRKKRRQRRRG (SEQ ID NO: 73), AWAC-CLAPGRKKRRQRRRG (SEQ ID NO: 74), AWLA-CLAPGRKKRRQRRRG (SEQ ID NO: 75), NWAA-CLAPGRKKRRQRRRG (SEQ ID NO: 76) and AWAACLAPGRKKRRQRRRG (SEQ ID NO: 77) are particularly preferred for use as inhibitors or modulators of the Rev protein and in particular for the Rev protein of HIV-1.

Such peptides are capable of interacting either generally with the Rev protein, or possibly with one of its domains. The proteins are generally characterized by the presence of different domains having functions which sometimes differ within their sequence. Depending on the three dimensional structure and the folding adopted by the protein, these domains are sometimes capable of being accessible to partners independently of each other.

This similar situation occurs for the various epitopes of a single protein allowing distinct monoclonal antibodies to be generated, the various epitopes being domains of the protein which are distinct from each other, and each being accessible.

A signal termed NES or nuclear export signal has been identified in the Rev protein, which ensures addressing of the protein outside the nucleus. This signal satisfies the definition of domain provided in the present application. For this reason, a peptide interacts either generally with the Rev protein or specifically with the NES domain of the Rev protein. The NES protein is defined by the sequence $^N$LQLPPLERLTLD$^C$ (SEQ ID NO: 8) in which a one-letter code represents the amino acid used.

In yet a further aspect, the present invention also concerns a family of interacting polypeptides of the invention or a population of interaction molecules of the invention, the members of the family/population being interacting polypeptides which only differ one from the other in the sequence of the heptapeptide motif.

Various members of the same family/population are thus identical as regards their penetration domain, their stabilization domain if they possess one, and their possible linkers. A family/population is defined by the presence of at least two members differing only in the sequence of the heptapeptide motif. However, a family generally comprises more than two members, in general at least 10 and preferably at least 50. Particularly preferred families within the context of the present invention are families comprising at least 100 distinct members, preferably 1000. This does not exclude a family or population having a certain number of members which are identical.

When the heptapeptide motif is constituted by 7 amino acids selected from the 20 natural amino acids, a family or population as defined in the present invention comprises up to $20^7$ distinct members.

The advantage of such a family is that only the heptapeptide motif is responsible for the different properties of each of the members of the family, given that it is the only variable of the members.

Preferably, an interacting polypeptide family of the present invention comprises the sequence $^NX_1X_2X_3X_4X_5X_6X_7$PGKKRRQRRRG$^C$ (SEQ ID NO: 6) in which the sequence $^NX_1X_2X_3X_4X_5X_6X_7^C$ corresponds to the sequence for the heptapeptide motif as defined in the invention and the sequence PGKKRRQRRRG (SEQ ID NO: 12) corresponds to the sequence for a linker and a cell penetration domain in which a one-letter code represents the amino acids used. $X_1$, $X_2$, $X_3$, $X_4$, $X_5$, $X_6$, $X_7$ represent amino acids. The heptapeptide domain is the only variable region in a polypeptide which is a member of the family (or population) compared with another polypeptides, also a member of the family.

More preferably, an interacting polypeptide family comprises members the sequence of which comprises or consists of the following sequence:

MSDQEAKPSTEDLGDKKEGEYIKLKVIGQDSSEIH-FKVKMTIHLKKLKESYCQRQGVPMNSLRFLFEGQR-IADNHTPKELGMEEEDVIEVYQEQTARPPNPKKEIE-LGGGGSX$_1$X$_2$X$_3$X$_4$X$_5$X$_6$X$_7$PGKKRRQRRRG (SEQ ID NO: 7), or the sequence MSDQEAKPSTEDLGDKKEGEY-IKLKVIGQDSSEIHFKVKMTHLKKLKESYCQRQGVP-MNSLRFLFEGQRIADNHTPKELGMEEEDVIEVYQEQ-TARGGGGSX$_1$X$_2$X$_3$X$_4$X$_5$X$_6$X$_7$PGKKRRQRRRG (SEQ ID NO: 78). The heptapeptide motif, corresponding to the sequence $^NX_1X_2X_3X_4X_5X_6X_7{}^C$, is the only region which differs from one member of the family to another. $X_1$, $X_2$, $X_3$, $X_4$, $X_5$, $X_6$ and $X_7$ represent amino acids.

The interacting polypeptides of this family are termed "SUMO-1 heptapeptide protein transduction domain", or SHP.

The sequence PGKKRRQRRRG (SEQ ID NO: 12) comprises the cell penetration domain for the polypeptides of the invention. A sequence having less than 3 modifications compared with this sequence is also a preferred sequence in the context of the invention. The term "modification" means addition of or removal of an amino acid, or substitution of an amino acid of this sequence by another amino acid.

The sequence:

MSDQEAKPSTEDLGDKKEGEY-IKLKVIGQDSSEIHFKVKMTTHLKKLKESYCQR QGVPMNSLRFLFEGQRIADNHTPKELG-MEEEDVIEVYQEQTARPPNPKKEIELGGGGS (SEQ ID NO: 16) comprises a stabilization domain for the interacting polypeptide. Another sequence comprising a stabilization domain is the sequence:

MSDQEAKPSTEDLGDKKEGEY-IKLKVIGQDSSEIHFKVKMTTHLKKLKESYCQR QGVPMNSLRFLFEGQRIADNHTPKELG-MEEEDVIEVYQEQTARGGGGS (SEQ ID NO: 79). Sequences sharing at least 80%, preferably at least 90% identity with said sequence are also sequences which may be used to constitute the stabilization domain of a family of polypeptides of the invention.

The invention also concerns all DNA sequences coding for a polypeptide of the invention, which are unique or form part of a family or population, or coding for any other fragment or domain mentioned in the present invention. It may be double stranded DNA or single stranded DNA. In the present invention, single stranded DNA is considered to code for a polypeptide when this sequence or the complementary sequence contains the coding portion. The DNA sequence is in the linear or circular form, for example in a plasmid.

The various RNAs which could be derived from transcription of a DNA sequence coding for a polypeptide of the invention are also included in the invention.

An interacting polypeptide as defined in the present invention has the potential capacity to interact with a protein partner, which may or may not be predetermined, to modify the behavior of the cell. Inside the cell, the presence of such a polypeptide may thus allow certain cell functions to be blocked, in particular by acting as competitive inhibitors. This action has therapeutic effects in a number of diseases if the cellular modification consists of attenuating or impeding a deleterious function in the cell. It is also envisaged that the presence of the polypeptide outside the cell modifies the property of the cell by interacting with a messenger or with a protein on the cell surface.

For this reason, the polypeptides of the invention as defined have an advantageous application in the field of therapy where they may be used as an active principle in drugs. They are often accompanied by various pharmaceutically acceptable excipients. The term "therapy" means both curative and prophylactic aims.

Interacting polypeptides of the invention specifically tested for their interaction with the Rev protein are more particularly preferred for use in therapy against infections by HIV, preferably in human therapy. The polypeptides of the invention may also be used in veterinary applications to treat animals infected with viruses which are homologues of HIV having a Rev protein or a close homologue. They may also be used preventatively.

Given that they are specially designed to have a means for penetrating cells, namely their penetration domain, they may be administered in various forms, without limitation. They may in particular be ingested in the form of Tablets, capsules or syrups, or be injected muscularly or intravenously, by penetration of a lotion, a gel or a pomade. Any other form of administration may also be envisaged. They may also be packaged in the form of liposomes then administered in that form.

It is not excluded that the drug could also consist of the DNA molecule coding for an interacting polypeptide of the invention. This is in particular the case when gene therapy is carried out.

The invention also concerns cells containing a polypeptide of the invention, on its own or forming part of a family, or any other fragment or domain mentioned in the present invention, and also cells containing DNA sequences coding for said polypeptides. Preferred cells are lymphocytes and macrophages, dendritic cells, Langerhans cells or stem cells; preferably, such cells are cells from mammals and in particular from humans. Other cells are yeast cells and bacterial cells.

The above types of cells may be obtained by transformation, gene therapy, or by contact of the cell and an interacting polypeptide of the invention. Such cells have particularly advantageous applications in therapy. Cells, in particular bacterial cells, transformed with a DNA coding for an interacting polypeptide of the invention, are particularly advantageous in producing said polypeptide. The polypeptide produced in bacteria is then optionally purified and may be used as an active principle in a drug.

In a further aspect, the present invention also concerns screening methods involving interacting polypeptides as described above. These polypeptides are specially designed to act against protein targets against which they have been tested.

A first screening method envisaged by the invention aims to identify polypeptides which are capable of modifying the phenotype of a cell.

The method comprises a step for bringing a polypeptide of the invention into contact with the cell the phenotype of which is to be modified. This step is followed by detection of the change of phenotype of the cell. These steps are optionally supplemented by a step for determining the sequence of the heptapeptide motif included in the sequence of the polypeptide which has been tested.

The term "phenotype" is used in its broad sense, encompassing all morphological or functional characteristics of the cell. A modification in the phenotype can in particular be characterized by a change in the shape of the cell, a modification in the composition of the membrane, secretion of a given protein, a change in color or a change in reactivity under given conditions.

The method aims to identify polypeptides which are capable of modifying, in a general manner, the phenotype of a cell; it may be an expected or desired modification. It may be a surprising modification or one which is not desired.

In accordance with one application of the method, it may be used to identify polypeptides which are capable of interacting with a given protein. In such a situation, the interaction of the polypeptide with its target could result in a modification of the phenotype which is expected, for example cell death, or resistance or sensitivity to an antibiotic, or to a virus, or to heat. Optionally, the interaction may be demonstrated via a reporter, in particular a reporter gene. That reporter element is responsible for the modification to the phenotype, that modification being expected.

The method may also be used to identify a polypeptide capable of interacting with a group of given proteins or, for example, with a metabolic pathway or a given immune cascade. In such a situation, the expected modification to the phenotype is modification of the function of the group or the modification of the pathway or the immune cascade. The effect of such a modification is not always determined in advance.

It is also possible to use the method of the invention to screen polypeptides to investigate, for example, a beneficial modification to a cell, without fixing the exact nature of the modification at the beginning of the screening method.

The first step of the method is characterized by bringing a polypeptide of the invention into the presence of the cell. The term "bringing into the presence" means both the action consisting of bringing the polypeptide into the proximity of the cell, contact and the action consisting of introducing the polypeptide into the cell. The expression "bringing into the presence" also includes the case in which the DNA coding for the polypeptide is introduced into the cell and this DNA is then translated to give rise to the polypeptide. In this situation, the cell itself contributes to generating the polypeptide.

The first step of the method is thus, for example, carried out by extracellular addition of the polypeptide to a medium containing the cell the phenotype of which is to be modified, for example by adding polypeptide to a fluid containing the cell. Since the polypeptide of the invention has a penetration domain, it may if necessary traverse the membrane of the cell.

The method described is either an extracellular screening method or an intracellular screening method. Screening is considered to be intracellular if the interaction between the polypeptide and its target takes place in the cell, independently of the fact that the polypeptide has been added in an extracellular manner or introduced in an intracellular manner. Screening is considered to be extracellular if in contrast the interaction between the polypeptide and its target takes place outside the cell, for example on its surface.

The screening method of the invention may be carried out in vivo, or in vitro. When it is carried out in vivo, the polypeptide and cell may be contacted by bringing the polypeptide into the presence of a fluid comprising the cell or a tissue containing said cell.

A particularly preferred application of the method of the invention consists in using a two-hybrid screening system. This application is recommended when the target protein for which a partner in the form of an interacting polypeptide is sought is known and its sequence has been determined. It is then possible to detect an interaction between the target protein and an interacting polypeptide of the invention. Such an interaction is generally manifested by induction of a reporter gene the expression of which modifies the phenotype in an easily detectable manner, for example by a change in the color of the cell.

A particularly preferred application of the method is in the field of screening novel interacting partners against viral proteins, including the Rev protein. Such a protein is found in various viruses, in particular HIV. In this application, the gene coding for the Rev protein is, for example, cloned into the two-hybrid system to act as the bait. Such a screen can identify polypeptides capable of rendering a cell resistant to infection by HIV, by preventing or limiting viral replication in the host cell.

A further application of the method consists of using a three-hybrid screening system. In such a system, two peptide partners the interaction of which is known are cloned into a two-hybrid system and a third plasmid comprises the interacting partner of the invention. This latter is tested for its capacity to modify the interaction between the two first partners. By dint of a reporter system for the two-hybrid screen, it is possible to observe and measure the action of the interacting partner on the interaction between the two peptide partners.

A second method which is encompassed by the present invention is a method for screening molecules to identify one of them which interacts with a predetermined intracellular target.

Such a method comprises a first step for generating polypeptides of the invention. The polypeptides thus generated are brought into the presence of the intracellular target, interactions between the polypeptide and target are detected, optionally followed by determination of the sequence of the heptapeptide motif of the polypeptide.

The polypeptide may be brought into the presence of the target directly by introduction of the polypeptide into the cell or indirectly by bringing the polypeptide into the presence of the cell, the polypeptide then penetrating into the cell.

The detection step may be carried out using any technique which is known to the skilled person. One detection type which may be envisaged is observation of a change in phenotype; the target may be adapted so that the modification of the phenotype is the result of expression of a reporter gene. Detection may also involve assay of an entity, for example assay of a protein or a metabolite.

The various preferred applications or characteristics mentioned in the context of the first method of the invention are also applicable to this second method. In particular, the method may be carried out in vivo or in vitro. It is preferably carried out using a two-hybrid system. Finally, a preferred application of such a screening method aims to identify interaction molecules capable of interacting with the viral proteins essential to replication of viruses, and more particularly the Rev protein of HIV.

The third method encompassed by the invention is a method for modulating the properties of an intracellular target molecule. Such a method comprises a step for bringing a cell which contains the target molecule into the presence of an interacting polypeptide of the invention.

The target molecule is preferably a protein or a fragment of protein comprising at least 5 amino acids, preferably at least 10. The polypeptide of the invention is specifically designed with a heptapeptide motif which is capable of interacting with the target molecule. Such a heptapeptide motif is advantageously determined by carrying out the first screening method of the invention.

The term "modulate properties" means any modifications to the target which may affect its function or its properties, in particular modifications which will modify its capacity to interact with its partners; and also modifications which will cause greater or lesser stability under certain conditions, modifications to the enzymatic kinetics, or to the specificity or selectivity.

As already mentioned, the various characteristics or preferred uses mentioned in the context of the first method of the invention are also applicable to the third method. In particular, the method may be carried out in vivo or in vitro. It is preferably carried out using a two-hybrid system. Finally, a preferred application of such a method aims to modify the properties of viral proteins essential to virus replication, and in particular the Rev protein of HIV.

In a further aspect, the invention concerns various uses. In particular, the invention comprises the use of a DNA sequence coding for a polypeptide of the invention so that the polypeptide then translated acts as prey in a phenotype screening; preferably, the DNA sequence is cloned into a two-hybrid system.

In fact, a two-hybrid system is characterized by investigation of an interaction between a given molecule (protein) generally termed the "bait" and a potential test partner, generally termed the "prey". A two-hybrid system generally comprises introducing into a cell sequences coding for the bait, the prey and a reporter gene specifically bound to other elements. In this context, the DNA sequence coding for a polypeptide of the invention may be used as the prey.

A particularly preferred situation in the context of the invention consists of using the DNA sequence coding for a polypeptide of the invention as a prey in the two-hybrid system. In this situation, a potential bait is the Rev protein of the human immunodeficiency virus (HIV). In fact, this viral protein is a particularly interesting target for the identification of novel inhibitors. The present invention thus more particularly envisages the use of the DNA sequence coding for a polypeptide of the invention in a two-hybrid system with the Rev protein of HIV.

As indicated above, the investigated interaction between the polypeptide of the invention and a given protein, for example HIV-Rev, may involve either all or a particular domain of the protein. In the context of the present invention, cloning as the bait only one sequence coding for a domain of the target protein is thus envisaged. This strategy allows interacting polypeptides specific to that domain to be identified.

In fact, the inventors have discovered that the interaction potentials between two given polypeptides are increased when the two polypeptides are comparable in size. The interacting polypeptide of the invention has a fairly short sequence responsible for interaction, namely the 7 amino acids of the heptapeptide, possibly with the combination of the interaction generated by the penetration motif. For this reason, the interacting polypeptides are particularly recommended because of their capacity to interact with polypeptides of comparable size, in a preferred manner, with comparably sized domains.

Particularly advantageous uses of interacting polypeptides in a two-hybrid system thus use, for the bait, sequences coding for domains of 5 to 30 amino acids, preferably 6 to 20, more preferably 7 to 15 amino acids. Such domains are, for example, binding domains, addressing signals or catalytic domains.

A further example of a particularly preferred domain in the context of these uses is the NLS (nuclear localization signal). A further preferred domain is the NES (nuclear export signal). Such a NES domain is particularly that of the Rev protein of HIV. Other "NES" signals are known which have sequences which are similar to a greater or lesser extent and sizes of the same order of magnitude. The two domains NLS and NES have sizes which are perfectly compatible with optimum sizes for interaction with a polypeptide of the invention.

A particular sequence for a NES domain is that of the Rev protein of HIV-1, LQLPPLERLTLD (SEQ ID NO: 8).

When the Rev protein of HIV is the target protein for which an interacting partner is sought, then it is particularly advantageous to clone a domain of the Rev protein into a two-hybrid screen, preferably the NES domain of rev, to act as the bait.

The present invention also concerns a screening method to identify, from candidate molecules, molecules which are capable of interacting with a given intracellular target. In accordance with this aspect of the invention, the interaction properties of the intracellular target with an interacting polypeptide of the invention are exploited. According to this method, a variation in this interaction between target and interacting polypeptide is to be detected when the candidate test molecule is added. A modification of the interaction between target and interacting polypeptide produces the potential capacity of the candidate molecule to interact with the intracellular target. In this application, the interacting polypeptide of the present invention, which is capable of interacting with a given intracellular target, acts as a tool for identifying novel drugs, which may or may not be protein-like in nature, which are also capable of interacting with the given intracellular target. The method thus comprises the following steps:
  i. bringing the target molecule into the presence of an interacting polypeptide of the invention;
  ii. detecting the interaction between the target molecule and the interacting polypeptide;
  iii. adding a candidate molecule;
  iv. detecting a modification to the interaction between the target molecule and the interacting polypeptide.

According to this method, it is possible to test different candidate molecules, in particular by high throughput screens. The interaction between the target molecule and the interacting polypeptide of the invention may be detected using any suitable means, in particular using a reporter gene. In conventional manner, a "two-hybrid" system is used. In such a situation, the interaction between the target molecule and the interacting polypeptide is detected using a reporter gene.

To carry out the method, once the target molecule is fixed, it may be advantageous, in a preliminary step, to identify an interacting polypeptide of the invention which is capable of interacting with said target molecule.

The present invention also encompasses the candidate molecules identified by this method, such as protein molecules, polynucleotides, small organic molecules having, for example, a molecular weight of less than 1000, lipids, glucides, etc.

In accordance with a particularly preferred implementation of the present invention, the intracellular target molecule is the Rev protein and the interacting polypeptide used is as defined in the present invention, preferably with one of the following heptapeptide sequences: $^N$FWFCGLK$^C$ (SEQ ID NO: 2), $^N$NWLCCLN$^C$ (SEQ ID NO: 3), $^N$FWFCGLA$^C$ (SEQ ID NO: 27), $^N$AWLCCLN$^C$ (SEQ ID NO: 25), and $^N$NWLCCLA$^C$ (SEQ ID NO: 26), FWFCGAK (SEQ ID NO: 45), FWFCGAA (SEQ ID NO: 46), NWACCLN (SEQ ID NO: 47), NWLACLN (SEQ ID NO:48), AWACCLN (SEQ ID NO: 49), AWLACLN (SEQ ID NO: 50), AWLCCLA (SEQ ID NO: 51), NWAACLN (SEQ ID NO: 52), NWACCLA (SEQ ID NO: 53), NWLACLA (SEQ ID NO: 54), AWAACLN (SEQ ID NO: 55), AWACCLA (SEQ ID NO: 56), AWLACLA (SEQ ID NO: 57), NWAACLA (SEQ ID NO: 58) and AWAACLA (SEQ ID NO: 59). As an example, the interacting polypeptide used is one of those described in the experimental section with the denomination SHPR.

The present invention also concerns a method for identifying molecules capable of modulating the properties of an intracellular target molecule. This method is in particular characterized by the following various steps:

In first step, nucleic acid molecules comprising sequences coding for various members of a family of interacting polypeptides of the invention are generated. These various members differ only in the sequence of the heptapeptide motif.

The method also comprises screening the molecules thus generated using a yeast two-hybrid system. In this system, use is made of the target molecule interacting partners for which are sought, as bait. The molecules generated act as the prey.

The method also comprises a step for detecting an interaction. This interaction may be manifested by the expression of a reporter gene included in the two-hybrid system. A phenotype change in the cell or assay of an entity can also allow detection of an interaction.

Optionally, the method also comprises verifying that interaction in a human cell. This step can be carried out in various manners. One manner consists of creating the equivalent of the two-hybrid system but adapted to human cells. The system is advantageously carried out using a cell line. Verifying the interaction by co-immunoprecipitation or verifying the effects caused by that interaction can also be envisaged. In this manner, the screened polypeptide is brought into the presence of the cell containing the intracellular target. It is observed whether this polypeptide induces an effect on the cell due to its interaction with the target.

A subsequent step which can also be envisaged consists of producing a quantity of interacting polypeptides identified in the context of the present invention. Such production is advantageously carried out in bacteria, for example by the action of an inducible promoter capable of over-expressing the polypeptide. The polypeptide may be produced in the soluble form or in the form of an inclusion body. Production in quantity in mammalian cells, for example Sf9 cells, may also be envisaged.

This method is particularly suitable for detecting interacting polypeptides capable of modifying the function of viral proteins, such as those of HIV: Tat, Rev.

In such a case, the method for obtaining and characterizing interacting polypeptides of the invention is carried out in several steps and may be carried out using the following methodology, employed by the inventors:

Screening of a Library of Random Heptapeptides in Yeast Against the Target Protein:

A library of random heptapeptides in fusion with the activating domain of a transcription factor, in this case GAL4, at its N-terminal end, and the nine amino acids of the basic Tat domain at its C-terminal end was constructed in a yeast expression vector. The sequence coding for the protein of interest, viral or cellular, is cloned downstream of that coding for a binding domain of DNA, in the present case LexA, in a vector allowing expression of the protein in the yeast The basic Tat domain associated with the heptapeptide motif is used as a motif ensuring intracellular penetration. The design of the final sequence of the protein is such that the various domains are spaced by the amino acids glycine or proline which ensures their separation. The L40 yeast strain which has the His and lacz reporter genes under the dependence of the binding motifs LexA is transformed by the vector expressing the target fusion LexA protein, which is carried out with the LexA-Tat, LexA-Rev and LexA-NES Rev proteins, then by the library of vectors having the random heptapeptides. The Tat and Rev proteins of HIV-1 are regulatory proteins essential to viral replication. A first selection of clones is carried out in histidine-free medium. The positive clones then undergo a β-galactosidase test on a filter.

The clearly positive colonies are recovered and the vector containing the heptapeptide motif isolated by transformation in *E. coli*. Sequencing the vector allows the heptapeptide motif to be identified.

Verification of Existence of Interaction in the Context of Mammalian Cells:

To ensure that the motifs selected in the yeast environment also function in the biochemical context of human cells, a similar test to that described above is carried out in HeLa cells. The heptapeptide motif is re-cloned from the yeast vector in a plasmid allowing expression in human cells downstream of the sequences coding for the Flag epitope, a nuclear localization signal and the activator domain of the protein Vp16.

This construct is co-transfected into HeLa cells with a vector expressing the LexA-target protein fusion and a vector having the reporter gene SEAP (secreted alkaline phosphatase) under the control of LexA binding sequences. Measurement of the SEAP activity allows the capacity of the heptapeptide motif to interact with the target protein in the nucleus of human cells to be evaluated. The vector expressing the heptapeptide motif also allowed evaluation by immunoblot experiments carried out with extracts of cells transfected by this construct, the level of expression of the fusion protein with this motif to be evaluated, and thus its stability in the cells to be verified. These experiments allowed confirmation of the capacity of several heptapeptide motifs to interact with Tat and Rev.

Association of the Heptapeptide/Basic Amino Acid Sequence of Tat with a Stabilization Protein:

Short linear peptides sometimes have poor stability in extra and intracellular media To overcome this problem, the inventors decided to associate the heptapeptide/basic Tat amino acid sequence with a small protein, which is stable and abundant in human cells. Their choice was initially focused on members of the ubiquitin family. The constructs were made with ubiquitin (ub) itself and a homologous protein, SUMO-1. The sequences coding for these proteins were introduced into an expression vector for mammalian cells. The heptapeptide/basic Tat amino acids sequence is introduced downstream of SUMO-1 or ubiquitin at a diglycine motif which is lost. This diglycine motif is normally bound to side chains of the lysines of proteins modified by said polypeptides. The proper expression of SUMO-1-specific Tat heptapeptide fusion proteins (SHPT) and Rev (SHPR) could be verified. For Ub constructs, these tests were not carried out in the absence of a good antibody directed against ubiquitin.

Using these constructs, the inventors carried out functional tests to evaluate whether SHPRs and SHPTs directed respectively against Rev and Tat were capable of preventing the function of these proteins. For Tat, the SHPT expression vectors were co-transfected with a vector expressing Tat and an indicator construct having the HIV-1 promoter in front of the CAT sequence. Two anti Rev SHPRs out of six demonstrated complete inhibition of the effect of Rev on a construct having the CAT sequence in association with the Rev response element (RRE) in an intron. The RNA RRE sequence allowed binding of the Rev protein. This type of indicative construct allowed an evaluation of the effect of Rev, which by causing transport towards the cytoplasm of the non spliced RNA, allowed expression of the CAT enzyme.

Production in Quantity of SHPT and SHPR Interacting Peptides:

Following these results, the inventors developed a system for producing interacting peptides in large quantities to be able to evaluate their capacity to penetrate into cells and to inhibit the function of their target protein starting from the extracellular medium. The anti-Rev SUMO-1-heptapeptide/basic Tat domain sequence was cloned into a vector allowing production in bacteria. A protocol for purification on a heparin column, then gel filtration, was defined. The first results showed that the SHPRs are produced in quantity and could be purified by this method.

Production of a large batch of these two molecules allowed the pharmaceutical importance of these proteins to be evaluated.

The whole process described here allows the feasibility of the method for identifying antagonist ligands of the target protein function to be established. The interacting peptides obtained may be used directly as therapeutic molecules, or they may act as models for the development of small organic molecules mimicking their structure.

The diagram shown in FIG. 1 recapitulates the various steps and constructs employed. The steps and constructs are given by way of example and can without any great difficulty be adapted or replaced by the skilled person by equivalents.

LEGEND TO FIGURES

FIG. 1: this shows the various steps and constructs employed to generate the interacting polypeptides capable of interacting with a given target protein. The double arrows indicate an interaction between two molecules.

The various types of cells are indicated for each step. Step 3 (functional tests) was carried out with viral Rev protein as the target.

FIG. 2: FIG. 2 shows maps of the various plasmids used for the yeast "two-hybrid" step.

FIG. 2A:

Plasmid pGAD-CR which derives from pGAD424.

Plasmid pGAD-CR-P which derives from pGAD-CR and includes the sequence coding for the heptapeptide motif inserted between the restriction sites BamHI and XmaI.

FIG. 2B:

Plasmid pLex-Tat, which contains Tat cDNA inserted between the restriction sites EcoRI and BamHI of the plasmid pLex9.

Plasmid pLexNES, which contains the sequence coding for the NES motif of Rev inserted between the restriction sites BamHI and XhoI of the plasmid pLex9.

Figure 2C:
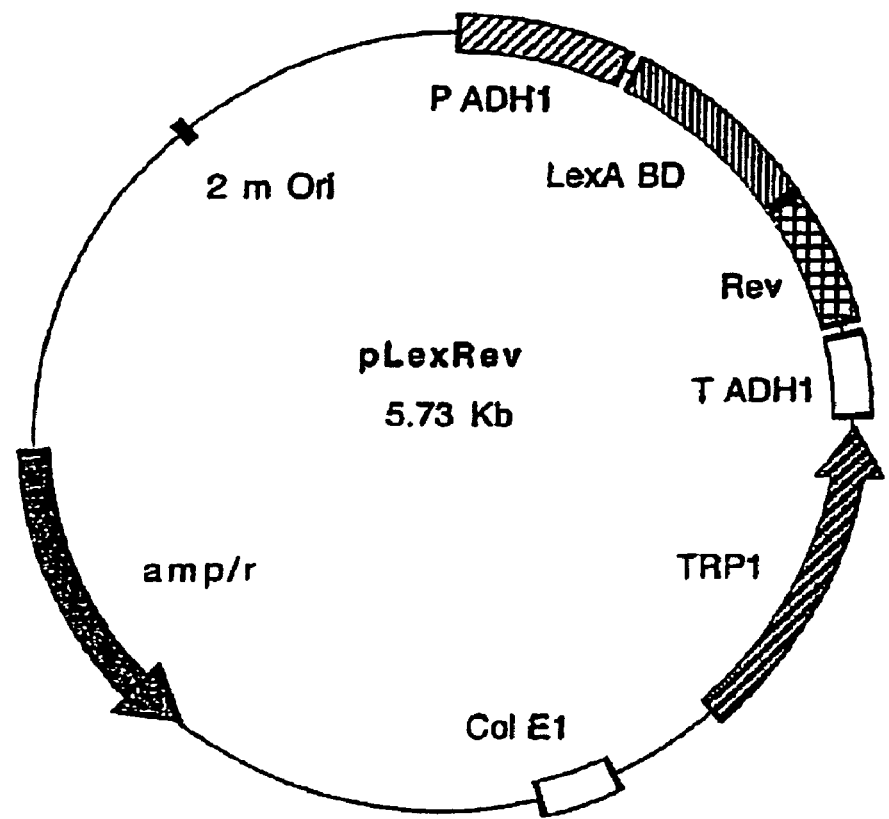

FIG. 2C: plasmid plexRev which contains Rev cDNA inserted between the restriction sites BamHI and SalI of the plasmid pLex9.

FIG. 3: FIG. 3 shows maps of various plasmids used for the two-hybrid step in mammalian cells.

FIG. 3A:

Plasmid pSG-FNV-P. The X7 PTD motif was amplified from pGAD-CR-P, digested with the restriction enzymes SalI and BglII then inserted between the restriction sites XhoI and BglII of the plasmid pSG-FNV.

Plasmid pSG5LexA-Tat, derived from pSG5LexA and includes Tat cDNA.

FIG. 3B:

Plasmid pSG5LexA-Rev, derived from pSG5LexA, and includes Rev cDNA.

FIG. 4: FIG. 4 shows maps of expression vectors SUMO-1-P for the functional tests.

pTL1-SUMO-1-CPP the sequence coding for SUMO-1 including the restriction sites XhoI and BglII has been inserted into pTL1.

pTL1-SUMO-1-P: the sequence for the X7 PTD motif has been inserted between the restriction sites XhoI and BglII of pTL1-SUMO-1-CP.

Figure 5:
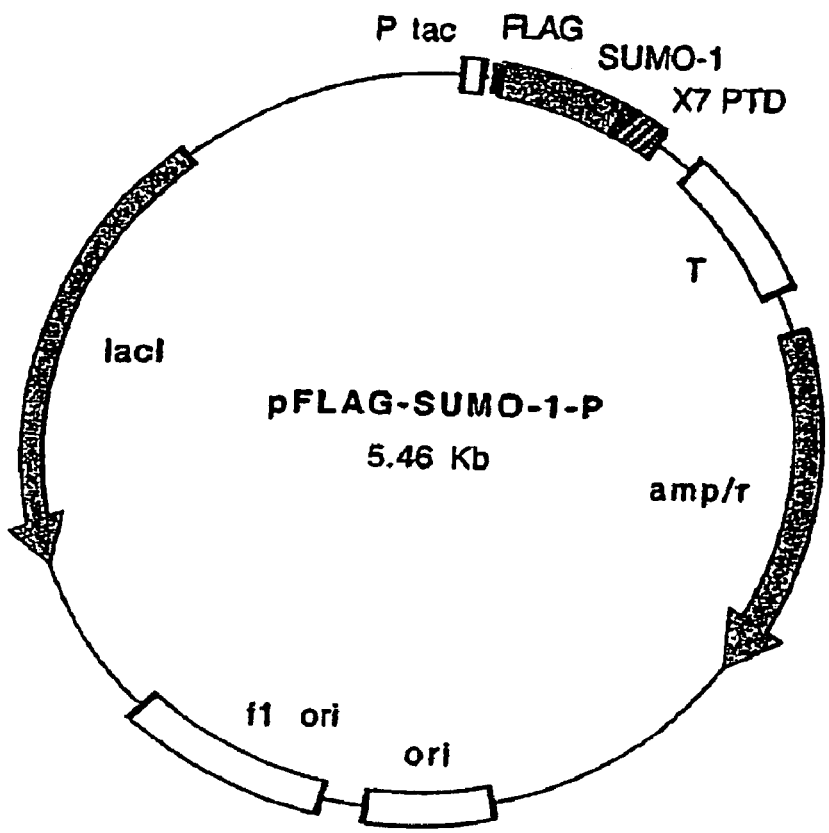

FIG. 5: FIG. 5 shows the map of the plasmid pFLAG-SUMO-1-P used as expression vectors in bacteria. This plasmid was constructed by inserting the sequence coding for the SUMO-1-P motif between the restriction sites HindIII and BglII of the plasmid pFLAG-MAC.

FIG. 6: FIG. 6 shows wild sequences of SUMO-1 (numbered 1) and of ubiquitin (numbered 3) as well as sequences for the interacting peptides of the invention comprising, as the stabilization domain, a fragment of SUMO-1 (interacting peptides SUMO, numbered 2) or ubiquitin (interacting peptides UB, numbered 4).

The sequences for the wild SUMO-1 and an interacting peptide comprising a fragment of SUMO-1 have been aligned. The star indicates the presence of an identical amino acid in the two sequences.

A similar alignment has been carried out between the sequence for ubiquitin and for the interacting peptide comprising a ubiquitin fragment.

The motif XXXXXXX in the interacting peptides represents the 7 amino acid sequence which may be defined in a random manner.

FIG. 7: FIG. 7 is a diagrammatic representation of proteins acting as bait (A) and prey (B, C) in two-hybrid tests in yeast (A) or in mammalian cells (C).
- A. The baits consist of the protein LexA in fusion with Tat (amino acids aa 1 to 86), Rev (aa 1 to 116) or the nuclear export signal of Rev (aa 70 to 96).
- B. The yeast preys comprise the activation domain GAL4, a series of 7 amino acids of random sequence and the transduction domain (protein transduction domain PTD) of Tat.
- C. The preys in mammalian cells include the FLAG epitope, the NLS (nuclear localization signal) of SV40 (wide T), the Vp16 activation domain of HSV and the heptapeptide+Tat PTD module.

Figure 8:
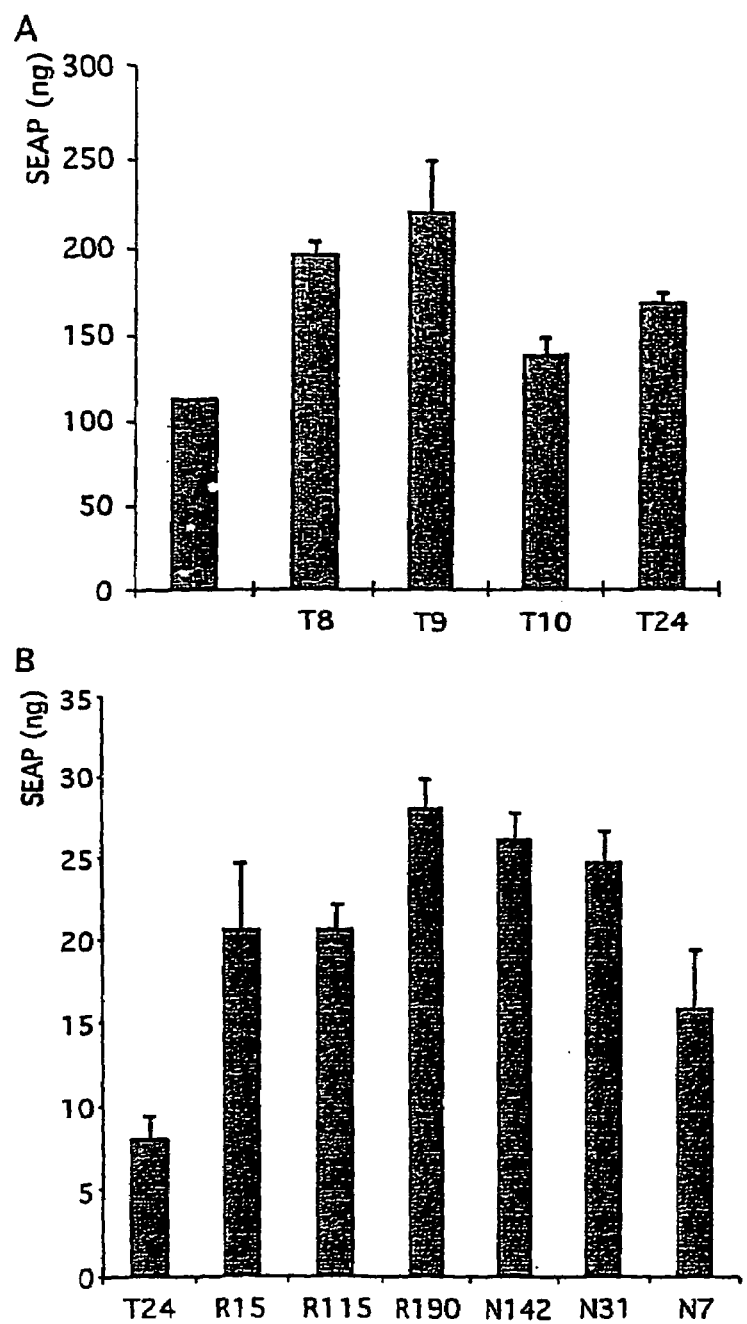

FIG. 8: FIG. 8 shows an analysis of the heptapeptide+Tat PTD modules, selected against Tat and Rev, by mammalian two-hybrid screening.
- A. HeLa cells are transfected with the reporter construct pSEAP Lex5X and pSG5LexA-Tat, alone or with pSG-FNV-P-T8, -T9, -T10 or -T24. The quantity of SEAP is measured and the mean of the values obtained for two independent points of the transfection is shown. The error bar corresponds to half the difference between the two values.
- B. The same test was carried out with pSEAP LEX5X and pSG5LexA-Rev together with pSG-FNV-P-T24, -R15, -R115, -R190, N-142, -N31 and -N7. The results are presented in the same manner as for FIG. 8A.

Figure 9:
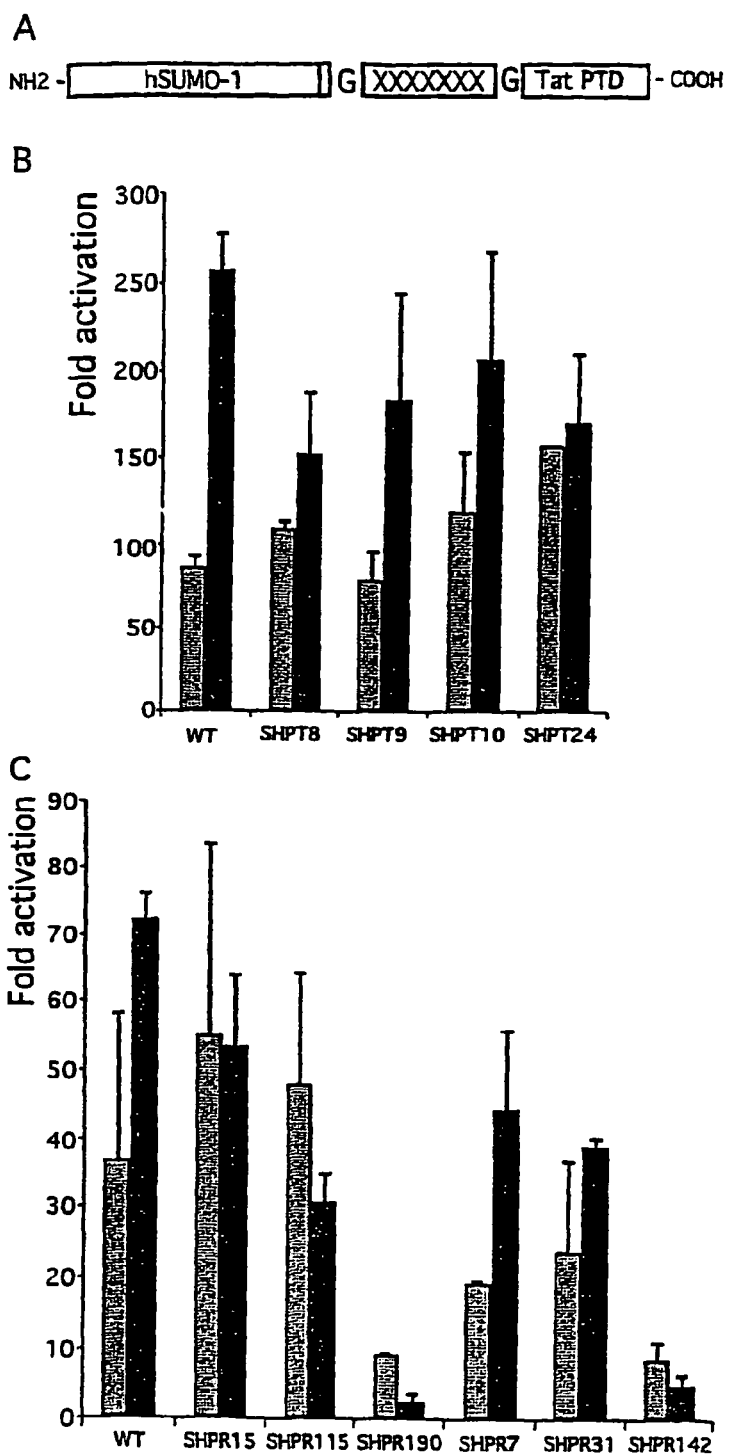

FIG. 9: FIG. 9 shows the inhibition of the activities of Tat and Rev for the constructs SHPT and SHPR.
- A. Diagrammatic representation of the construct SHP which includes the entire sequence of SUMO-1, in which the diglycine motif (GG) has mutated to AR, associated at its C-terminal end with the heptapeptide-Tat PTD module.
- B. HeLa cells were transfected with the construct LTR HIV-CAT with pSG-Tat and either pTL1-SUMO-1, pTL1-SHPT-8, -9, -10 or -24. The quantity of these latter plasmids was either 0.5 µg (pale gray bars) or 2 µg (dark gray bars). The CAT activity was measured and the mean of the values obtained for two independent points of transfection is shown. The error bar corresponds to half the difference between the two values.

C. To evaluate the Rev activity, HeLa cells were transfected with plasmids pDM128 and pSG-Rev together either with pTL1-SUMO-1, pTL1-SHPR-15, -115, -190, -R7, -R31 and -R142. The CAT activities are shown in the same manner as for FIG. 9B.

Figure 10:
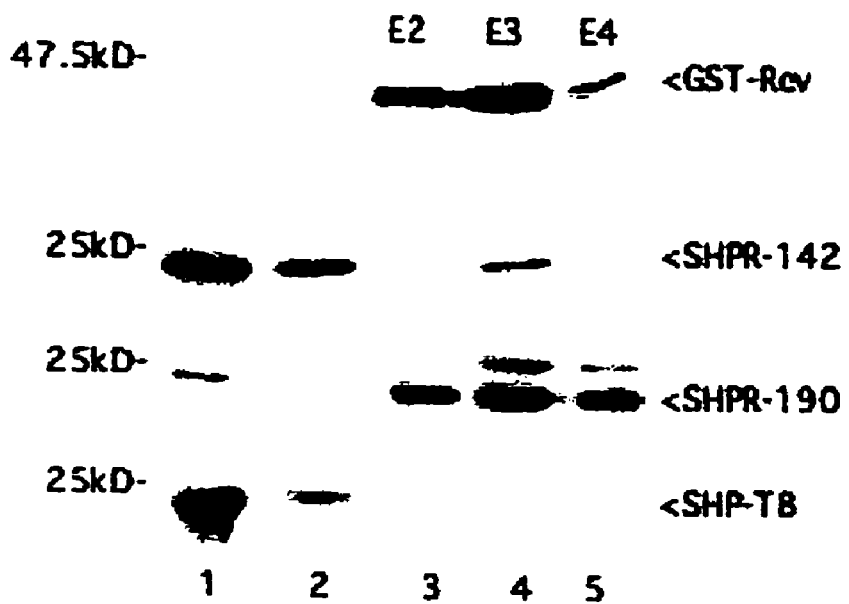

FIG. 10: FIG. 10 shows the direct protein-protein interaction between SHPR and Rev. GXT-Rev was produced in bacteria and loaded onto an agarose-glutathion column. SHPR-142, -190 and SHPT-8 were loaded into the column. After rinsing, the proteins were eluted with glutathione. An aliquot of the feed (line 1), rinse (line 2) and elution (lines 3, 4, 5) fractions was analyzed by immunoblot for GST-Rev (top graph) and for SHP using antibodies against GST or against FLAG respectively. This shows that SHPR-142 and SHPR-190 co-eluted with GST-Rev, while SHPR-8 did not bind to the protein on the column.

Figure 11:
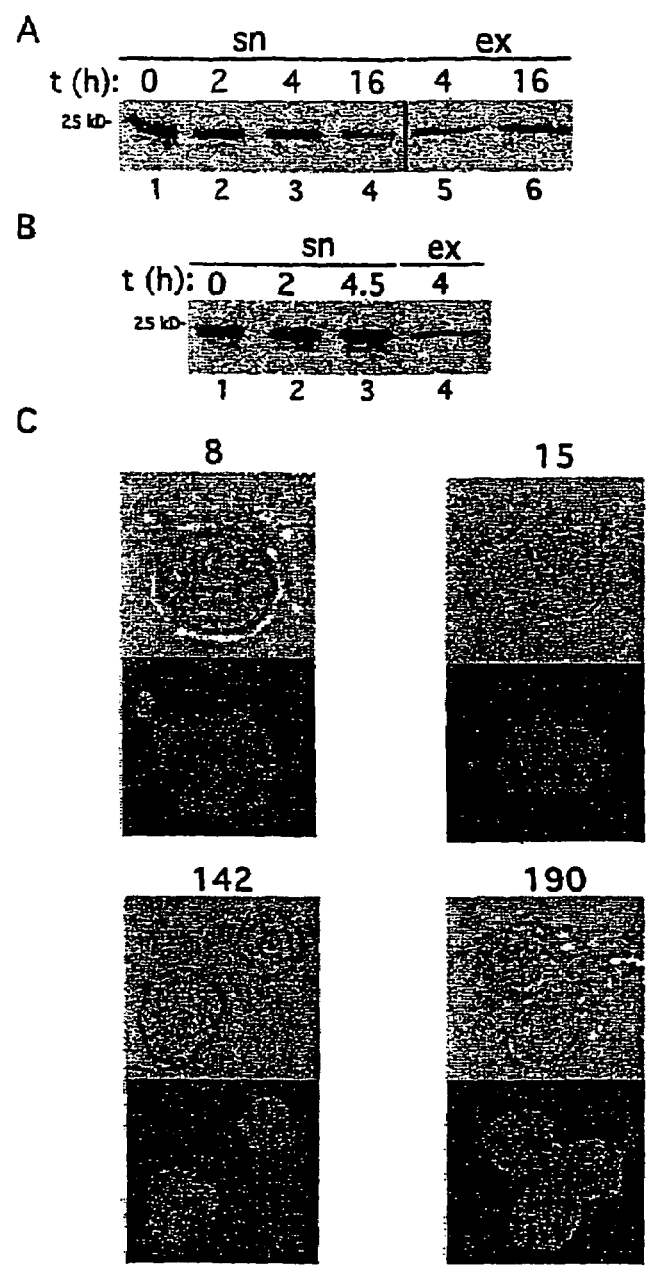

FIG. 11: FIG. 11 shows the intracellular entry of SHP.

Mononuclear cells were prepared from peripheral blood, either directly (A) or after activation with PHA (phytohemagglutinin) and IL-2 (interleukin 2) (B), then incubated with 2 µM of SHPR-190. At the times indicated after addition of the interacting peptide, an aliquot of supernatant was analyzed by immunoblot using antibodies against FLAG (A, lines 1 to 4; B, lines 1 to 3). The cells were collected and lysed in RIPA buffer. The extract obtained was analyzed by immunoblot as described for the supernatant (A, lines 5 and 6; B, line 4). In portion A, the exposure times were different between lines 5 and 6 (30 s) and lines 1 to 4 (5 s).

These analyses show that the protein is stable in the supernatant and also that it is present inside the cells.

In part C, Jurkat cells were incubated with 2 µM of SHPT-8, SHPR-15, SHPR-142 or SHPR-190 for one hour and 24 h later the cells were collected and analyzed by immunofluorescence using an antibody against FLAG. Light transmission and fluorescence images are shown for representative cells. The cells had a diffuse fluorescence which was not observed for the controls.

Figure 12:
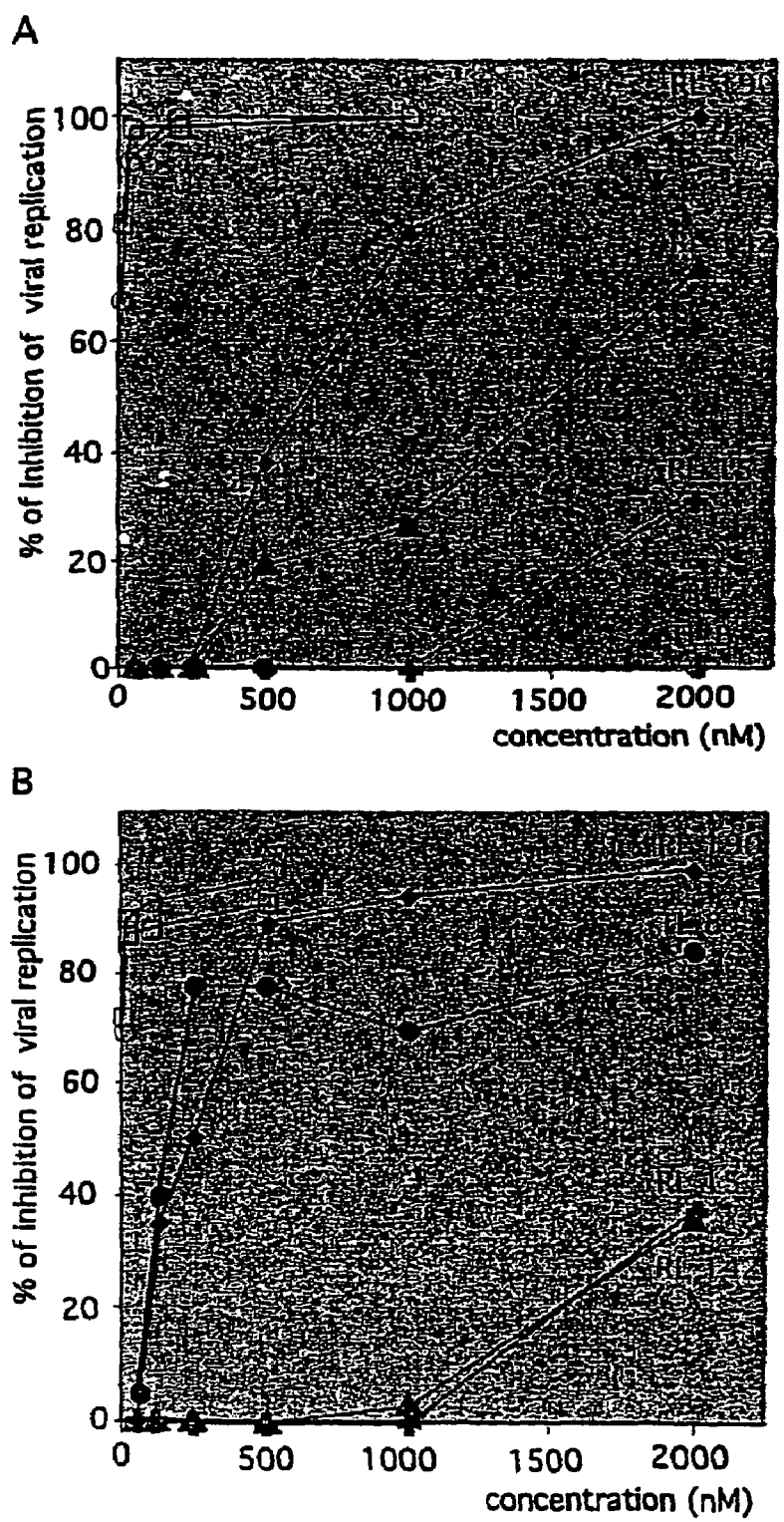

FIG. 12: FIG. 12 shows the inhibition of replication of HIV-1 in lymphocytes and macrophages.
  A. Mononuclear cells were prepared from peripheral blood and activated. The cells were treated with different quantities of AZT, indinavir, SHPR-15, -142, -190 or SHPT-8 and infected with HIV-1-LAI. Viral replication was measured by assaying the reverse transcription activity in the supernatants and the percentage inhibitions are shown as a function of the quantity of compound.
  B. Macrophages were prepared from monocytes, treated with different concentrations of drugs and SHPs and infected with HIV-1/Ba-L. Viral replication was measured by assaying reverse transcription activity. The percentage inhibitions at 7 days post infection are shown in the same manner as for FIG. 12A.

EXAMPLES

Example 1

Description of Constructs and Operating Conditions used to Identify Peptides Interacting with Tat and Rev Proteins of HIV-1

HIV-1 expresses several regulating proteins the action of which on essential cellular factors ensures the rapid and effective production of viral particles. After two decades of intense research, significant advances have been made in understanding the molecular mechanisms inducing the various actions of these regulating proteins. Particular interest has been paid to two of them, namely the Tat and Rev proteins.

Tat activates transcription of the integrated provirus by establishing contacts with the transcription factors and the TAR motif located at the 5' end of the viral RNA.

Rev also has the dual capacity of interacting with RNA, in this case the RRE motif present in the intronic position in the 3' portion of the viral RNA, and with nuclear factors of the cell. This viral protein includes both a nuclear localization signal (NLS) and a nuclear export signal (NES) and by acting as a shuttle between the nucleus and the cytoplasm, this protein allows export and thus translation of unspliced and partially spliced viral RNA.

Because Tat and Rev are small proteins which act via protein-protein interaction, the inventors estimated that it should be possible to inhibit their function, which is absolutely necessary to viral replication, using peptide ligands (interacting peptides) capable of interfering competitively with associations in which these proteins of interest are engaged.

Since it can show up interactions in the intracellular medium, in particular in the nucleus, the double hybrid (or two-hybrid) test represents a method of choice for a first step in selecting such interacting peptides.

An important problem linked to the use of peptides is their intracellular penetration. To avoid using complex gene therapy procedures, the inventors added the cell penetration property at the screening step, by adding a protein transduction domain, more particularly in this case the basic Tat domain. This method allowed the inventors to identify short peptide sequences which bind to Tat or Rev. The association of these peptide sequences with SUMO-1 to stabilize them produced small proteins denoted SUMO-1 heptapeptide protein transduction domains or SHP, which are capable of penetrating effectively into lymphocytes and some of them are capable of inhibiting the functions of Rev. These proteins, for which it has also been observed that they inhibit viral replication, both in lymphocytes and in macrophages, represent novel potential therapeutic agents for use in combating the generation of new viral particles.

The SHPs developed against the Tat protein are termed SHPT and those developed against the Rev protein are termed SHPR.

I. Yeast Two-Hybrid System:

A. Random Peptide Library:

1—pGAD-CR Construct:

This plasmid was a derivative of pGAD424 (clontech). This vector was digested with EcoRI and BglII.

The fragment containing the linker regions, the cloning sites for the random sequence and the basic Tat domain was obtained by hybridizing the following oligonucleotides:

```
5' pAATTGGGTGGTGGCGGATCCGGTTTGCCCGGGAGAAAGAAGCGTAG
ACAAAGAAGACGTGGTTA (SEQ ID NO: 17)
CCCACCACCGCCTAGGCCAAACGGGCCCTCTTTCTTCGCATCTGTTT
CTTCTGCACCAATTCTAGp5' (SEQ ID NO: 18)
```

(p signifies phosphate). This fragment was inserted between the EcoRI and BglII sites of pGAD424.

2—Construction of Library of Interacting Peptides (pGAD-CR-P):

The random sequence fragment was generated by hybridizing the following two oligonucleotides:

```
5'-bACTCGGATCCNNNNNNNNNNNNNNNNNNNNNNNCCCGGGGTCGCAGTG
(SEQ ID NO: 19)
GGCCCCAGCGTCACb-5', (SEQ ID NO: 20)
```

(b signifies biotin), repair with DNA polymerase and digestion with the enzymes BamHI and XmaI. The digestion product was mixed with paramagnetic streptavidin beads to extract the biotinylated ends.

The BamHI-XmaI fragment contained in the supernatant was inserted between the BamHI and XmaI sites of the pGAD-CR vector to produce the plasmids pGAD-CR-Ps.

The ligation products were transformed in the XL1-blue *E. coli* strain and streaked onto LB agar plates containing ampicillin. $2 \times 10^6$ independent colonies were recovered and cultured for 1 h in LB medium containing ampicillin. The plasmids were then extracted and purified using the standard PEG procedure.

B. Baits 1. pLex9 Vector:

This vector was a derivative of pGBT9 (Clontech). The binding domain of GAL4 DNA was replaced with that for LexA (Farjot et al, 1999).

2. Construction of pLex-Tat:

The repaired NcoI/BamHI fragment obtained from the pSG-Tat vector (Veschambre et al, 1995) was cloned between the SmaI and BamHI sites of pLex9.

3. Construction of pLexRev and pLex-NES:

These constructs contained the whole Rev sequence (plexRev) or only that of the NES (pLex-NES) in fusion with that of LexA (Farjot et al, 1999).

The two-hybrid screenings with either pLexTat, pLexRev or pLex-NES as bait and pGAD-CR-P as prey were carried out in the HF7c strain of *S. cerevisiae* as already described (Rousset et al, Oncogene, 1998, 16, 643-654). The colonies were cultivated on histidine-free minimum medium, and were analyzed for expression of β-galactosidase by assay on filter as previously described (Rousset et al, Oncogene, 1998, 16, 643-654). The plasmids pGAD-CR-P of positive colonies were recovered and the heptapeptide motif was sequenced.

II. Mammalian Cell Two-Hybrid System:

A. pSG-FNV-P Constructs:

These constructs are derivatives of the plasmid pSG-FNV (Desbois et al, 1996). The region containing the heptapeptide was amplified from pGAD-CR-P constructs using the following oligonucleotides:

```
5'-TGAAGGTCGACCACCAAACCCAAAAAAAGAG-3'   (Oligo 5')
(SEQ ID NO: 30)

5'-CCTGAGAAAGCAACCTGACC-3'              (Oligo 3')
(SEQ ID NO: 31)
```

The PCR fragment was digested with SalI and BglII and inserted between the XhoI and BglII sites of the pSG-FNV vector, producing the plasmid pSG-FNV-P.

B. Baits

1. Construction of Vector pSG-LexA-Rev

This vector is a derivative of pSG5 (Green et al, 1988) expressing in mammalian cells the fusion LexA-Rev (Farjot et al, 1999).

2. Construction of Vector pSG-LexA-Tat:

The sequence coding for Tat was introduced downstream of that for LexA into pSG-LexA.

C. Indicator Construct (Reporter Construct)

This plasmid had the SEAP sequence under the control of five binding sites for LexA (Farjot et al, 1999).

III. Expression Vectors SUMO-1 and SUMO-1-Peptides for Mammalian Cells:

A. Wild pTL1-SUMO-1 Construct:

The SUMO-1 sequence was amplified from a cDNA (IMAGE clone obtained from HGMP-UK) using the following oligos:

```
5'-GGGTCGACGTCCATATGTCTGACCAGGAGG-3'
(SEQ ID NO: 32)

5'-AAAAGATCTCTAAACTGTTGAATGACC-3'
(SEQ ID NO: 33)
```

The amplified fragment was digested with SalI and BglII and inserted between the XhoI and BglII sites of the expression vector pTL1 which is a derivative of pSG5.

b. Construction of vector pTL1-SUMO-CP:

This construct allowed heptapeptides in fusion with SUMO-1 to be inserted, replacing the diglycine motif. The SUMO-1 sequence was amplified with the following oligonucleotides:

```
5'-GGGTCGACGTCCATATGTCTGACCAGGAGG-3'
(SEQ ID NO: 34)

5'-ATCAGATCTGAATCTCGAGCCGTTTGTTCCTGATAAAC-3'
(SEQ ID NO: 35)
```

The amplified fragment was digested with SalI and BglII and inserted between the XhoI and BglII sites of the vector pTL1.

C. Construction of Vectors pTL1-SUMO-P

The sequence containing the heptapeptide and the basic Tat domain was amplified as described in II.A, digested with SalI and BglII and inserted between the XhoI and BglII sites of the vector pTL1-SUMO-CP.

IV. Ubiquitin and Ubiquitin Peptide Expression Vectors for Mammalian Cells:

A. pTL1-Ub-CP Construct:

The sequence for ubiquitin was amplified from a cCNA (IMAGE clone obtained from HGMP-UK) using the following oligonucleotides:

```
5'-CTAAGAATTCAAAATGCAAATCTTCGTGAAAACC-3'
(SEQ ID NO: 36)

5'-CACGAAGATCTACACTCGAGCTCTCAGACGCAGGACC-3'
(SEQ ID NO: 37)
```

The amplified fragment was digested with EcoRI and BglII and inserted between the EcoRI and BglII sites of pTL1.

B. Construction of Vectors pTL1-Ub-P

The sequence containing the heptapeptide and the basic Tat domain was amplified as described in II.A, digested with SalI and BglII and inserted between the XhoI and BglII sites of pTL1-Ub-CP.

V. Construction of Bacterial Expression Vectors in pFLAG-SUMO-P:

The pTL1-SUMO-P plasmids were digested by HindIII and BglII. The fragment containing the SUMO-1 sequence in fusion with the heptapeptide/basic Tat domain portion was inserted between the HindIII and BglII sites of the pFLAG-Mac vector (IBI FLAG® Biosystems).

VI. Construction of Bacterial Expression Vectors in pFLAG-Ub-P:

The PTL1-Ub-P plasmids were digested with EcoRI and BglII. The fragment containing the Ub sequence in fusion with the peptide/basic Tat domain portion was inserted between the EcoRI and BglII sites of the vector pFLAG-2 (IBI FLAG® Biosystems).

VI. Cell Culture and Transfection:

HeLa and COS7 cells were cultivated in DMEM medium supplemented with 5% fetal calf serum in a moist atmosphere containing 5% $CO_2$. The transfections were carried out using the calcium/phosphate co-precipitation method.

For the two-hybrid tests in mammalian cells, transfection was carried out in 6-well plates seeded with 80000 HeLa cells. The DNA mixture contained 125 ng of the SEAP reporter construct, 25 ng of the Tat or Rev expression vectors in fusion with LexA, with a quantity defined as optimum of plasmid expressing the prey, namely 250 ng for the motifs selected against Tat and 25 ng for the motifs selected against Rev, with the exception of clones 142 and 190 (50 ng). The SEAP activity was measured using the "SEAP reporter gene assay chemiluminescent" kit (Roche) following the manufacturer's instructions. The Tat functional test was carried out by transfecting 300000 HeLa cells in 60 mm Petri dishes with the reporter construct LTR HIV-CAT (50 ng), pSG-Tat (2 ng) and the expression vector for SUMO-1 or an interacting peptide (0.5 and 2 μg). The Rev functional test was carried out in a similar manner by transfecting the reporter plasmid pDM128 (50 ng), pSG-Rev (5 ng) and the expression vector for SUMO-1 or an interacting peptide (0.5 and 2 μg). The CAT activity was measured using the CAT ELISA kit (Roche). Jurkat cells were cultivated in RPMI 1640 supplemented with 10% fetal calf serum at 37° C. in a moist atmosphere containing 5% $CO_2$. Human peripheral blood mononuclear cells (PBMC) and monocytes were isolated from the blood of healthy seronegative donors by density gradient centrifugation using a Ficoll-Hypaque technique (Eurobio). The human peripheral blood mononuclear cells (PBMC) were activated for 3 days with 1 μg of phytohemagglutinin-P (PHA-P, Difco Laboratories) and 5 IU/ml of human recombinant interleukin-2 (rhIL-2, Roche Products). Next, Human peripheral blood mononuclear cells (PBMC) were disposed on a 96 well microplate (10000 cells per well) in 200 μl of medium A (RPMI 1640 cell culture medium; Invitrogen, 10% fetal calf serum (FCS, Bio West) inactivated by heat (+56° C. for 45 minutes) and 1% of tri-antibiotic mixture (penicillin, streptomycin and neomycin; PSN, Invitrogen) supplemented with 20 IU/ml of rhIL-2. The cells were maintained at 37° C. in a moist atmosphere with 5% $CO_2$.

The monocyte-derived macrophages (MDM) were differentiated from monocytes at 7 days by adherence. On day 3, 300000 cells per well were dispersed in 48-well plates in 1 ml of culture medium. Monocyte differentiation and MDM culture was carried out in cell culture medium A': DMEM Glutamax™ supplemented with 10% heat inactivated FCS and PSN tri-antibiotic mixture 1× at 37° C. in a moist 5% $CO_2$ atmosphere.

VIII. Production of Bacteria and Purification of SHPs

The vectors described in section VI were used to transform BL21-CodonPlus™-RP (Stratagene) *E. coli* cells which had been cultivated in 2 l of LB medium to an optical density of 0.9. After 30 minutes at 18° C., 0.1 mM of IPTG was added to the cultures which were continued overnight at 18° C. The bacteria were sonicated in a lysis buffer: 200 mM of NaCl, 0.1 M of tris-HCl, pH 7.4, 10 mM of $MgCl_2$ which was supplemented with "complete" antiprotease from Roche (Complete antiprotease, Roche), 0.5 mg/ml of lysosyme and 20 u/ml of benzonase (Sigma). After centrifuging at 4000 rpm for 30 minutes, the supernatant was loaded onto a 5 ml heparin HyperD column (Biosepra). Elution was carried out with a DE 600 buffer (600 mM of KCl, 20 mL of Hepes, pH 7.9, 10 μM of $ZnCl_2$, 1.5 mM of $MgCl_2$, 1 mM of EDTA and 1 mM of DTT). The elution product was fractionated on a Hiload 16/60 Superdex 200 gel filtration column (Amersham Pharmacia Biotech). The fractions containing the SHPs were combined and, after dialysis against a DE 50 buffer (same composition as DE 600 buffer, with the exception of the KCl concentration which was 20 mM), loaded onto a 5 ml mono Q HyperD column (Biosepra). The flow-through was dialyzed against PBS 1× buffer, concentrated 10 times by freeze drying and sterile filtered.

IX—Immunoblot and Immunofluorescence

The techniques used were those conventionally used in the field (polyacrylamide gels, difluorinated polyvinylidene membranes, PVDF, monoclonal antibody directed against FLAG from SIGMA, diluted 1:1000 and revealing with the ECL kit from Amersham Biosciences).

The immunofluorescence tests were carried out with a primary anti-FLAG antibody in a dilution of 1:500 incubated for 2 hours and a secondary antibody coupled to the Alexa Fluor 488 fluorophore (Molecular Probes) diluted 1:1000, incubated for one hour.

X. Virus and Antiviral Test:

PBMC cells were infected with the lymphotropic strain with reference HIV-1-LA1 (Barre-Sinoussi et al, Science, 1983, 220, 868-871) and MDM cells with the reference strain having tropism for the macrophages HIV-1/Ba-L (Gartner et al, Science, 1086, 233, 215-219). These viruses were amplified in vitro with umbilical blood mononuclear cells (UBMC) activated with PHA-P. The cell-free supernatant was centrifuged at 360000 g for 10 minutes to eliminate soluble factors, and the residue was re-suspended in cell culture medium. Virus stocks were titrated using PBMC cells activated with PHA-P and 50% tissue culture infectious doses (TCID50) were calculated using Kärber's formula.

PBMC cells were pre-treated for 30 minutes by 5 concentrations of each molecule and infected with 75 TCID50 of the HIV-1-LA1 strain. AZT (1.6, 8, 40, 200 and 1000 nM) and indinavir (1.6, 8, 40, 200 and 1000 nM) were used as the control. The interacting peptides SHPR-8, -15, -190 and SHPT-142 were tested at concentrations of 31, 62.5, 125, 250, 500, 1000 and 2000 nM. The molecules were maintained throughout culture, and the cellular supernatant was harvested 7 days post infection and stored at −20° C. to measure viral replication by reverse transcriptase activity (RT) assay. The PBMC cells were observed on a microscopic level on the seventh day to detect any cytotoxicity induced by the drug.

The MDM cells were pre-treated for 30 minutes in 6 concentrations of different molecules and infected with 30000 TCID50 of the HIV-1/Ba-L strain. AZT (0.8, 4, 20, 100 and 500 nM) and indinavir (0.8, 4, 20, 100 and 500 nM) were used as the control. The interacting peptides SHPR-8, -15, -190 and SHPT-142 were tested at concentrations of 62.5, 125, 250, 500, 1000 and 2000 nM. The molecules were maintained for 7 days post infection, and the cellular supernatant was harvested 7, 14 and 21 days post infection and stored at −20° C. to measure viral replication by reverse transcriptase activity (RT) assay. The MDM cells were observed on a microscopic level on days 7, 14 and 21 to detect any cytotoxicity induced by the drug.

HIV replication was analyzed by assaying the RT activity in the supernatants from cell cultures using the RetroSys RT kit (Innovagen). The experiments were carried out 3 times and the results are expressed as the mean of the RT activity±the standard deviation (SD). The 50%, 70% and 90% effective doses (ED50, ED70, ED90) were calculated using the percentage from the untreated controls and software (J and T C Chou, Biosoft, Cambridge).

Example 2

Results

Identification of Peptide Sequences Binding to Tat and Rev

The search for interacting peptides against the regulation proteins Tat and Rev was carried out initially by two-hybrid yeast system screening. The baits contained the sequence for LexA in fusion with the entire sequence of Tat, Rev or NES of Rev (FIG. 7A). The prey comprised 3 different portions: the GAL4 activation domain, a random sequence of 7 amino acids and the Tat transduction domain (FIG. 7B). The library of expression vectors for the preys was constructed by cloning DNA fragments prepared from synthetic oligonucleotides including a series of 21 degenerate positions.

This library was used in 3 different screenings with either LexTat, LexRev or LexNES as the bait (see Table 1a). All of the vectors of the clones cultivated in a histidine-free medium and positive to the test for β-galactosidase were isolated and re-tested. None of these vectors triggered expression of β-galactosidase when LexA alone was used as bait (see Table 1b, c, d). Four vectors selected against Tat, 3 against Rev and 19 against NES were then obtained (see Table 1 b, c, d). These positive clones were analyzed using a two-hybrid test in mammalian cells. The constructs produced were described above and are shown in FIG. 1C. When LexA, alone or with prey proteins, was expressed in a transitional manner, no expression of secreted alkaline phosphatase (SEAP) was observed from the reporter construct. Both LexTat and LexRev are themselves capable of triggering expression of SEAP, but this production is increased by co-transfection with prey vectors. The results are shown in FIG. 8. They show that sequences selected on yeast are also capable of binding to Tat and Rev proteins in the nucleus of human cells.

TABLE 1a

Number of clones obtained by two-hybrid screening of the random peptide library:

| Bait | LexTat | LexRev | LexNES |
|---|---|---|---|
| Number of transformates | $15.5 \times 10^6$ | $9.3 \times 10^6$ | $2.5 \times 10^5$ |
| Number of colonies growing on histidine-free plates | 94 | 161 | 40 |
| Number of positive colonies for expression of β-gal | 24 | 12 | 19 |

TABLE 1b

β-galactosidase test for clones obtained from screening carried out with LexTat as bait:

Colony color
W = white after 6 h; B = blue after 6 h
BB = blue after 3 h; BBB = blue after 1 h

| Clone no | pLex9 | pLexTat |
|---|---|---|
| 8 | W | BB |
| 9 | W | BB |
| 10 | W | BB |
| 24 | W | BBB |
| Others | W | W |

TABLE 1c

β-galactosidase test for clones obtained from screening carried out with LexRev as bait:

Colony color
W = white after 6 h; B = blue after 6 h
BB = blue after 3 h; BBB = blue after 1 h

| Clone no | pLex9 | pLexRev |
|---|---|---|
| 15 | W | B |
| 115 | W | B |
| 190 | W | BB |
| Others | W | W |

TABLE 1d

β-galactosidase test for clones obtained from screening carried out with LexNES as bait:

Colony color
W = white after 6 h; B = blue after 6 h
BB = blue after 3 h; BBB = blue after 1 h

| Clone no | pLex9 | pLexNES |
|---|---|---|
| 1 | W | B |
| 7 | W | BB |
| 9 | W | BB |
| 17 | W | B |
| 21 | W | BB |
| 25 | W | BB |
| 31 | W | BB |
| 123 | W | BB |
| 124 | W | B |
| 127 | W | BB |
| 130 | W | BB |
| 131 | W | B |
| 136 | W | BB |
| 137 | W | BBB |
| 138 | W | BB |
| 141 | W | BB |
| 142 | W | BBB |
| 147 | W | BB |
| 151 | W | BBB |
| Others | W | W |

Inhibition of Tat and Rev Functions

Given the capacity of the interacting peptides isolated in the preceding steps, the next step was to verify their capacity to act as antagonist for Tat and Rev activity, affecting their association with cellular effectors. Thus, functional tests were carried out. To stabilize the identified interacting peptides, constructs were produced with the SUMO-1 protein. The entire coding sequence, including a mutation in the diglycine C-terminal motif, was inserted upstream of the sequence coding for the heptapeptide transduction domain module. The artificial or chimeral proteins so produced were denoted SUMO-1-heptapeptide-protein transduction domain Tat or Rev, i.e. SHPT or SHPR depending on their capacity to bind to Tat or Rev respectively.

The effect of the 4 SHPTs on the transactivation of the HIV-1 promoter by Tat was evaluated by transitory expression experiments in HeLa cells. At low concentrations, the various SHPTs did not reduce Tat transactivation; at higher concentrations, a slight reduction in transactivation was observed, in particular with SHPT-8 (see FIG. 9A). These data show that the selected SHPTs were not very good inhibitors of the Tat function.

The SHPR activity was evaluated using the reporter construct pDM128 which included the coding sequence CAT and an RRE motif in an intron. Expression of Rev stimulated expression of CAT allowing an unspliced messenger to be exported to the cytoplasm. Using this test, it was observed that the various SHPRs had different activities; the results are shown in FIG. 9B. The data clearly show that 2 SHPRs, SHPR-142 and SHPR-190, were a priori effective inhibitors of the function of Rev. It was verified whether this inhibition was in fact directly correlated with a protein-protein interaction as predicted. To this end, both Rev and the SHPRs were produced in bacteria. A protocol was developed to purify the SHPs (see Example 1). Rev was expressed in fusion with GST and coupled to glutathione-agarose beads. SHPR-142 and SHPR-190 were loaded onto the column, as well as SHPT-8 as a control. When the GST-Rev fusion was discharged with the glutathione, co-elution of SHPR-142 with SHPR-190 was observed while no SHPT was present in fractions containing GST-Rev (see FIG. 10). This shows that the interaction between SHPR-142 and SHPR-190 and with Rev is direct and does not involve an intermediate.

Penetration of SHPs into Cells from Extracellular Medium

The activity of SHPs identified from the extracellular medium was then tested. Firstly, the cytotoxicity was examined. At concentrations of up to 1 µM, these molecules did not appear to modify the percentage of cells dying in a population of peripheral blood mononuclear cells (PBMC) cultivated in vitro, activated with PHA and IL-2.

To evaluate the capacity of SHPs to penetrate into cells, PBMCs were cultivated in medium supplemented with 2 µM of SHPR-190. At different times, an aliquot of supernatant was removed and the cells were collected. After washing several times, the cells were lysed in RIPA buffer and the supernatant as well as that which was extracted was analyzed by immunoblot using an antibody directed against the FLAG eiptope, which is present at the N-terminal end of SHP produced in bacteria. Both for resting lymphocytes (FIG. 11A) and activated lymphocytes (FIG. 11B), it was observed that SHPR-190 was stable in the culture medium and that a fraction of the protein was present inside the cell (FIG. 11). By assuming that a lymphocyte is a sphere 12µ in diameter, quantification experiments which were carried out with antibodies labeled with a fluorophore showed that an external concentration of 2 µM resulted in an intracellular concentration of 15 µM. This indicates that SHPs are capable of being concentrated inside the cell.

To confirm that SHPs do indeed enter the cell, immunofluorescence analyses were also carried out. Jurkat cells were incubated with 1 µM of SHP for 4 hours and after washing twice, the cells were cultured for 24 hours. Immunofluorescence analysis using an antibody against FLAG showed a substantial fluorescence present in a diffuse manner in the whole inside of the cell for the 4 test SHPs (FIG. 11C) while this was not the case for the control cells.

The experiments thus prove that lymphocytes may be cultivated with purified SHPs and that these molecules may enter the cells.

Inhibition of Replication of HIV-1 by SHPs

In a last step, it was examined whether SHPs were actually capable of inhibiting HIV-1 replication. This was carried out in PBMCs activated by PHA-P and in MDMs. In the model of PBMC activated by PHA-P, replication of HIV-1-LA1 was optimum on the $7^{th}$ day. The effects of different SHPs was thus tested at this time. AZT and indinavir were used as controls. As predicted, replication of HIV-1-LA1 was effectively inhibited by AZT and indinavir (FIG. 12A and Table 2a). SHPT-8 did not have any anti-HIV activity and SHPR-15 had a low activity. In contrast, SHPR-142 and SHPR-190 reduced replication in PBMC cells activated with PHA-P. Replication of HIV-1 was reduced by SHPR-142 at 2 µM (73±6%, see Table 2a) and by SHPR-190 at 1 and 2 µM (80±7% and 100% respectively, see Table 2a). Comparison of the 50% effective doses confirms that SHPR-190 is more active than SHPR-142 (see Table 2b).

TABLE 2a

Anti-HIV effects of AZT, indinavir IDV and SHPR-15, SHPT-8, SHPR-142 and SHPR-190 in PBMCs infected with HIV-1 LA1. Percentage inhibition.

|  | Dose | Mean | SD |
|---|---|---|---|
| AZT | 1.6 | 0 | — |
|  | 8 | 81 | 17 |
|  | 40 | 98 | 1 |
|  | 200 | 98 | 1 |
|  | 1000 | 100 | 0 |
| IDV | 1.6 | 0 | — |
|  | 8 | 67 | 7 |
|  | 40 | 92 | 6 |
|  | 200 | 100 | 0 |
|  | 1000 | 100 | 0 |
| #8 | 31 | 0 | — |
|  | 62.5 | 0 | — |
|  | 125 | 0 | — |
|  | 250 | 0 | — |
|  | 500 | 0 | — |
|  | 1000 | 0 | — |
|  | 2000 | 0 | — |
| #15 | 31 | 0 | — |
|  | 62.5 | 0 | — |
|  | 125 | 0 | — |
|  | 250 | 0 | — |
|  | 500 | 0 | — |
|  | 1000 | 0 | — |
|  | 2000 | 31 | 13 |
| #142 | 31 | 0 | — |
|  | 62.5 | 0 | — |
|  | 125 | 0 | — |
|  | 250 | 0 | — |
|  | 500 | 19 | 10 |
|  | 1000 | 26 | 19 |
|  | 2000 | 73 | 6 |
| #190 | 31 | 0 | — |
|  | 62.5 | 0 | — |
|  | 125 | 0 | — |
|  | 250 | 0 | — |
|  | 500 | 38 | 17 |
|  | 1000 | 80 | 7 |
|  | 2000 | 100 | 0 |

TABLE 2b

Anti-HIV effects of AZT, indinavir IDV and SHPR-142 and SHPR-190 in PBMCs infected with HIV-1-LA1: 50%, 70% and 90% of effective doses. The results are expressed in nM.

|  |  | 7$^{th}$ day |
|---|---|---|
| AZT | ED50 | 11 |
|  | ED70 | 13.5 |
|  | ED90 | 19 |
| IDV | ED50 | 14 |
|  | ED70 | 18 |
|  | ED90 | 25.5 |
| SHPR-142 | ED50 | 1400 |
|  | ED70 | 2100 |
|  | ED90 | 4600 |
| SHPR-180 | ED50 | 615 |
|  | ED70 | 720 |
|  | ED90 | 927 |

The reference strain HIV-1/Ba-L replicated effectively in MDM (monocyte-derived macrophages). The reverse transcription activity in the culture supernatant was detected from the 7$^{th}$ day post infection (pi) and was a maximum between 14 and 21 days pi. As predicted, HIV-1/Ba-L replication was reduced in a dose-dependent manner by AZT and indinavir (FIG. 12B and Table 3a). In these cells, as in PBMCs, SHPR-15 showed a very low activity. In contrast to the results obtained for activated PBMCs, SHPT-142 also presented a slight inhibition of HIV replication (44±10% for 2 µM on day 14, and not effect at 1 µM, Table 3a). In contrast, viral replication was inhibited by both SHPT-8 and SHPR-190 at 2 µM (69±6% and 92±2% on day 14 respectively, Table 3a). In contrast to SHPT-8, the effects of SHPR-190 on HIV replication was dose-dependent (FIG. 12B). Further, as shown by the ED90 values (Table 3b), the interacting peptide SHPR-190 had a higher anti-HIV activity. These effects declined after 14 days, probably due to degradation of the interacting peptide.

TABLE 3a

Anti-HIV effects of AZT, indinavir IDV and SHPT-8 and SHPR-190 in MDMs infected by HIV-1/Ba-L. Percentage inhibition.

|  |  | Day 7 | | Day 14 | | Day 21 | |
|---|---|---|---|---|---|---|---|
|  |  | Mean | SD | Mean | SD | Mean | SD |
| AZT | 0.8 | 76 | 5 | 0 | — | 0 | — |
|  | 4 | 72 | 18 | 55 | 24 | 0 | — |
|  | 20 | 87 | 2 | 82 | 7 | 68 | 9 |
|  | 100 | 88 | 4 | 92 | 4 | 81 | 12 |
|  | 500 | 93 | 2 | 100 | 0 | 100 | 0 |
| IDV | 0.8 | 59 | 25 | 0 | — | 0 | — |
|  | 4 | 69 | 10 | 0 | — | 0 | — |
|  | 20 | 90 | 3 | 68 | 7 | 47 | 16 |
|  | 100 | 93 | 3 | 100 | 0 | 96 | 1 |
|  | 500 | 97 | 0 | 100 | 0 | 100 | 0 |
| #15 | 62.5 | 0 | — | 0 | — | 0 | — |
|  | 125 | 0 | — | 0 | — | 0 | — |
|  | 250 | 0 | — | 0 | — | 0 | — |
|  | 500 | 0 | — | 0 | — | 0 | — |
|  | 1000 | 0 | — | 0 | — | 0 | — |
|  | 2000 | 37 | 31 | 3 | 15 | 0 | — |
| #8 | 62.5 | 5 | 17 | 0 | — | 0 | — |
|  | 125 | 39 | 16 | 2 | 5 | 5 | 6 |
|  | 250 | 78 | 6 | 55 | 9 | 37 | 8 |
|  | 500 | 78 | 6 | 50 | 8 | 21 | 8 |
|  | 1000 | 70 | 10 | 46 | 1 | 20 | 9 |
|  | 2000 | 84 | 1 | 69 | 6 | 59 | 0 |
| #142 | 62.5 | 0 | — | 0 | — | 0 | — |
|  | 125 | 0 | — | 0 | — | 0 | — |
|  | 250 | 0 | — | 0 | — | 0 | — |
|  | 500 | 0 | — | 0 | — | 0 | — |
|  | 1000 | 3 | 14 | 0 | — | 0 | — |
|  | 2000 | 35 | 9 | 44 | 10 | 18 | 11 |
| #190 | 62.5 | 0 | — | 0 | — | 0 | — |
|  | 125 | 34 | 7 | 0 | — | 0 | — |
|  | 250 | 50 | 4 | 0 | — | 0 | — |
|  | 500 | 89 | 8 | 66 | 4 | 28 | 16 |
|  | 1000 | 94 | 3 | 70 | 9 | 50 | 5 |
|  | 2000 | 99 | 0 | 92 | 2 | 60 | 3 |

The results thus show that the interacting peptide SHPR-190 has genuine anti-HIV effects in the two principal cellular targets of HIV, namely T CD4+ lymphocytes and macrophages.

Further, given that the peptide SHPR-142 was selected against NES from Rev and that the peptide SHPR-190 was also shown to interact with the NES signal from Rev, these two molecules potentially interfere with the export properties of the Rev protein.

TABLE 3b

Anti-HIV effects of AZT, indinavir IDV and SHPT-8 and SHPR-190 in MDMs infected with HIV-1/Ba-L: 50, 70 and 90% of effective doses. The results are expressed in nM.

|  |  | Day 14 | Day 21 |
|---|---|---|---|
| AZT | ED50 | 3 | NC |
|  | ED70 | 9 | NC |
|  | ED90 | 64 | NC |
| IDV | ED50 | 22 | 22 |
|  | ED70 | 26.5 | 32 |
|  | ED90 | 34.5 | 62 |
| SHPT-8 | ED50 | 1100 | NC |
|  | ED70 | 2050 | NC |
|  | ED90 | 5500 | NC |
| SHPR-190 | ED50 | 850 | 1200 |
|  | ED70 | 1040 | >2000 |
|  | ED90 | 1450 | >2000 |

"NC" means not calculated.

Example 3

Identified SHP Sequences

SHPT:

SHPT-8   Phe Thr Met Arg Gly Val Asp
         (SEQ ID NO: 38)

SHPT-9#  Ile Thr Arg Arg Ile Glu Met Pro Gly Arg
         Asp Ile Pro Gly Val Asp Gly Ser Ile Leu
         Arg Gly Cys Trp Asp (SEQ ID NO: 39)

SHPT-10- Gly Ala Val Asp Lys Ser His
         (SEQ ID NO: 40)

SHPT-24  Ser Arg Val Asp Arg Lys Asp
         (SEQ ID NO: 41)

: this clone resulted from insertion of several heptapeptide sequences.

SHPR:

| | | |
|---|---|---|
| SHPR-15 | Met Cys Val Asp Leu Leu Leu | (SEQ ID NO: 42) |
| SHPR-31 | Arg Gln Val Gly Met Leu Tyr | (SEQ ID NO: 43) |
| SHPR-115 | Leu Ala Pro Arg Asn Leu Leu | (SEQ ID NO: 44) |
| SHPR-142* | Phe Trp Phe Cys Gly Leu Lys | (SEQ ID NO: 2) |
| SHPR-190* | Asn Trp Leu Cys Cys Leu Asn | (SEQ ID NO: 3) |

*: these two heptapeptides are those with an inhibiting effect on the function of the Rev protein.

Example 4

Mutations in SHPR-142 and SHPR-190

Mutation analyses were carried out to best determine the action mechanism of SHPs directed against Rev and the importance of residues at each position in SHPR-142 and -190.

1. Effect of Binding of SHPR-Rev on Binding of Viral Protein to its RNA Target Sequence, the Rev Response Element (RRE):

The Rev protein causes export of HIV-1 mRNA towards the cytoplasm by binding to a particular RNA sequence: the RRE. The inventors thus answered the question of whether binding of SHPR inhibitors of Rev interfered with this Rev/RRE association. To this end, gel retard experiments were carried out with a RNA molecule corresponding to the RRE element as the probe. The Rev protein produced in bacteria binds to this RNA and induces a non denaturing polyacrylamide gel migration retardation. Adding SHPR-190 and -142 proteins did not inhibit this association, but induced a larger retardation, indicating that the SHPR-Rev complex is still capable of binding to RRE.

In these experiments, addition of a control protein such as SHPT-8 had no particular effect.

Thus, it may be concluded from these experiments that SHPR inhibitors-190 and -142 do not modify the interaction of Rev with the element RRE. Their inhibiting action must rather be due to export of the Rev-RRE complex towards the cytoplasm. This point is in agreement with the observation that SHPR-190 and -142 interacts with Rev NES.

2. Sequences Required for the Inhibitor Activity of SHPR-142 and -190:

The following experiments were carried out by the inventors:

- During cloning of the heptapeptide motif downstream of the SUMO-1 sequence, about ten amino acids coding for the GAL4 (PPNPKKEIEL (SEQ ID NO 80)) had been conserved in order not to modify the immediate environment of the selected binding motif.
- Mutants (termed ΔGAL4) of SHPR-142 and -190 were produced where this sequence coding for a short GAL4 motif had been eliminated.
- To evaluate the contribution of each of the amino acids of the heptapeptide motif with an inhibitor activity, each of the seven positions of the SHPR-142 and -190 was mutated to alanine (Ala) and the mutants were tested to look for mutants having enhanced anti-viral activity.

These various mutants were tested using a transitory expression system consisting of transfecting HeLa cells of the reporter plasmid having the CAT sequence associated with the RRE in the intronic position with expression vectors for the Rev protein and the SHPR protein. The inhibitor activity of these SHPR derivatives was measured and is shown in the following Tables compared with that of parental SHPR The values indicated correspond to the mean of those obtained for two independent measurements. The separation between the two values was less than 20%.

TABLE 4

| | Activity/SHPR142 (%) | Activity/SHPR190 (%) |
|---|---|---|
| Mutant AA1/Ala | 116% | 17% |
| Mutant AA2/Ala | 233% | 264% |
| Mutant AA3/Ala | 171% | 76% |
| Mutant AA4/Ala | 148% | 73% |
| Mutant AA5/Ala | 109% | 525% |
| Mutant AA6/Ala | 71% | 129% |
| Mutant AA7/Ala | 31% | 40% |
| Mutant ΔGAL4 | 24% | 31% |

Table 4: Expression vectors in mammalian cells of SHPR-142 (column 2) and SHPR-190 (column 3) were mutated at each of the positions of the heptapeptide (changed to alanine) and by deletion of amino acids coding for GAL4. These vectors were transfected with the reporter plasmid pDM128 and the expression vector Rev as described in the above sections (and in Roisin et al, JBC (2004) 279: 9208). The quantity of CAT protein is expressed as a % of that corresponding to transfection of parental SHPR. A value of more than 100 thus indicates a negative effect on the inhibiting power of SHPR and a lower value indicates an increase in this inhibiting property.

TABLE 5

| | Activity/SHPR-190 (%) |
|---|---|
| Mutant ΔGAL4 | 31% |
| Mutant ΔGAL4 + AA1/Ala | 7% |
| Mutant ΔGAL4 + AA4/Ala | 15% |

Table 5: The expression vector of SHPR was modified by deleting amino acids coding for GAL4 and modified in positions 1 or 4 of the heptapeptide. These expression vectors were tested as described in the legend to Table 4.

These results show that the sequence coding for the amino acids of GAL4 play a negative role. For the 142 sequence, modification of the first five residues had a negative effect; that of amino acids 6 and 7 increase the activity, especially for position 7 (Table 4). For the −190 heptapeptide, it appears that substitution of amino acid 1 increases the activity fairly significantly, although to a lesser degree than that for positions 3, 4 and 7 (Table 4). Further, mutation in the 1 position or the 4 position further increases the effect of eliminating GAL4 sequences (Table 5).

It may be concluded from these results that the residual portion GAL4 may be eliminated from final hybrid proteins. For the −190 heptapeptide, it also advantageously appears to modify position 1.

A modification in position 4 could also be advantageous with the aim of limiting the quantity of cysteine residues. These may cause modifications by oxidation. By considering the results obtained for the two motifs-142 and -190, it appears that the tryptophan residue in the 2 position is important and that it needs a nearby cysteine residue which may be in the 4 position or, preferably, in the 5 position.

These results lead to novel derivatives of SHPR-190 which are potentially more active.

Studies were also carried out to better discern the role of the transduction domain. To this end, the basic Tat domain, used for SHPR-142 and -190, was either truncated to delete the major portion or replaced by a polyarginine motif. In both cases, it was shown that the intracellular capacity of the polypeptide to interact with its Rev target was conserved. These results confirm the essential nature of the heptapeptide to the capacity to interact with the target, in which interaction the transduction domain does not participate.

For this reason, if a polypeptide of the invention is identified for its capacity to interact with a given target, it is then possible to vary the transduction domain to optimize its properties (effectivity of transduction, safety, non-immunogenicity, etc) without modifying the heptapeptide, while ensuring that the polypeptide obtained is always capable of interacting with the given target.

REFERENCES

Desbois C, Rousset R, Bantignies F and Jalinot P (1996). Exclusion of Int-6 from PML nuclear bodies by binding to the HTLV-1 Tax oncoprotein. Science 273, 951-3;

Farjot G, Sergeant A and Mikaelian I (1999). A new nucleoporin-like protein interacts with both HIV-1 Rev nuclear export signal and CRM-1. J Biol Chem 274, 17309-17;

Green S, Issemann, I, and Sheer, E (1988). A versatile in vivo and in vitro eukaryotic expression vector for protein engineering. Nucleic Acids Res 16, 369;

Veschambre P, Simard P and Jalinot P (1995). Evidence for functional interaction between the HIV-1 Tat transactivator and the TATA box binding protein in vivo. J Mol Biol 250, 169-80;

Wender P A, Mitchell D J, Pattabiraman K, Pelkey E T, Steinman L, Rothbard J B (2000). The design, synthesis and evaluation of molecules that enable or enhance cellular uptake: peptoid molecular transporters. Proc Natl Acad Sci USA, 97 (24): 13003-8;

Kräber G, Beitrag zur kollektiven Behandlung Pharmakologischer Reihenversuche [contribution regarding the collective treatment of serial pharmacological investigations] (1931) Arch Exp Path Pharmak 162, 956-959.

The invention claimed is:

1. An interacting polypeptide comprising the following elements:
   (a) a heptapeptide motif with the sequence $^{N}X_1WX_3X_4X_5X_6X_7^{C}$ in which $X_1$, $X_3$, $X_4$, $X_5$, $X_6$ and $X_7$ are amino acids independently selected from natural or modified amino acids, in which $X_4$ and/or $X_5$ is a cysteine and in which W is tryptophan;
   (b) a transduction domain; and
   (c) a stabilization domain which is a fragment of ubiquitin or SUMO-1, the amino acid sequence of which fragment comprises SEQ ID NO.:1 or SEQ ID NO.:15;
   characterized in that it is a chimeric polypeptide, in that the amino acid $X_7$ is 5 to 35 amino acids from the C-terminal end of said polypeptide, in that domain (b) is located C-terminally with respect to motif (a), and in that the stabilization domain (c) is located N-terminally with respect to the heptapeptide motif of said polypeptide.

2. An interacting polypeptide according to claim 1, characterized in that said motif has a sequence defined by a random process.

3. An interacting polypeptide according to claim 1, characterized in that linkers are inserted between said elements (a) and (b) and/or (a) and (c).

4. A polypeptide according to claim 3, characterized in that said linkers are sequences containing less than 5 amino acids and comprising at least 20% of the amino acids glycine or proline.

5. A polypeptide according to claim 1, characterized in that the transduction domain is that of the HIV-Tat protein.

6. A polypeptide according to claim 5, characterized in that said transduction domain comprises the sequence RKKRRQRRR (SEQ ID NO: 9).

7. A polypeptide according to claim 1, characterized in that said stabilization domain comprises the sequence:
MSDQEAKPSTEDLGDKKEGEY-IKLKVIGQDSSEIHFKVKMTTHLKKLKE-SYCQRQGVPMNSLRFL FEGQRIADNHTPKELG-MEEEDVIEVYQEQT (SEQ ID NO: 1).

8. A polypeptide according to claim 1, characterized in that the amino acid $X_7$ is between 10 and 30 amino acids from the C-terminal end of said polypeptide.

9. A polypeptide according to claim 8, characterized in that the amino acid $X_7$ is between 15 and 25 amino acids from the C-terminal end of said polypeptide.

10. A polypeptide according to claim 1, in which the cysteine is preferably in the $X_5$ position.

11. A polypeptide according to claim 1, comprising as motif (a) a sequence selected from the following sequences: FWFCGLK (SEQ ID NO: 2), NWLCCLN (SEQ ID NO: 3), FWFCGLLA (SEQ ID NO: 27), AWLCCLN (SEQ ID NO: 25), NWLCCLLA (SEQ ID NO: 26), FWFCGAK (SEQ ID NO: 45), FWFCGAA (SEQ ID NO: 46), NWACCLN (SEQ ID NO: 47), NWLACLN (SEQ ID NO:48), AWACCLN (SEQ ID NO: 49), AWLACLN (SEQ ID NO: 50), AWL-CCLA (SEQ ID NO: 51), NWAACLN (SEQ ID NO: 52), NWACCLA (SEQ ID NO: 53), NWLACLA (SEQ ID NO: 54), AWAACLN (SEQ ID NO: 55), AWACCLA (SEQ ID NO: 56), AWLACLIA (SEQ ID NO: 57), NWAACLA (SEQ ID NO: 58) and AWAACLA (SEQ ID NO: 59).

12. A polypeptide according to claim 11, comprising a sequence selected from the following sequences: FWFCGLKPGRKKRRQRRRG (SEQ ID NO: 4), NWL-CCLNPGRKKRRQRRRG (SEQ ID NO: 5), FWFCGAK-PGRKKRRQRRRG (SEQ ID NO: 60), FWFCGLAPGRKKRRQRRRG (SEQ ID NO: 61), FWFC-GAAPGRKKRRQRRRG (SEQ ID NO: 62), AWLCCLN-PGRKKRRQRRRG (SEQ ID NO: 63), NWACCLN-PGRKKRRQRRRG (SEQ ID NO: 64), NWLACLNPGRKKRRQRRRG (SEQ ID NO: 65), NWL-CCLAPGRKKRRQRRRG (SEQ ID NO: 66), AWACCLN-PGRKKRRQRRRG (SEQ ID NO: 67), AWLACLN-PGRKKRRQRRRG (SEQ ID NO: 68), AWLCCLAPGRKKRRQRRRG (SEQ ID NO: 69), NWAA-CLNPGRKKRRQRRRG (SEQ ID NO: 70), NWAC-CLAPGRKKRRQRRRG (SEQ ID NO: 71), NWLLA-CLAPGRKKRRQRRRG (SEQ ID NO: 72), AWAACLNPGRKKRRQRRRG (SEQ ID NO: 73), AWAC-CLAPGRKKRRQRRRG (SEQ ID NO: 74), AWLA-CLAPGRKKRRQRRRG (SEQ ID NO: 75), NWAA-CLAPGRKKRRQRRRG (SEQ ID NO: 76) and AWAACLAPGRKKRRQRRRG (SEQ ID NO: 77).

13. A polypeptide comprising a heptapeptide with the sequence: $^{N}X_1WX_3X_4X_5X_6X_7{}^{C}$, in which $X_1$, $X_3$, $X_4$, $X_5$, $X_6$, and $X_7$ are amino acids selected independently from natural or modified amino acids, in which $X_4$ and/or $X_5$ is a cysteine, and W is tryptophan, and interacting with Rev protein or one of its domains, in which the sequence of the heptapeptide is selected from the following sequences: FWFCGLK (SEQ ID NO: 2) NWLCCLN (SEQ ID NO: 3), FWFCGLA (SEQ ID NO: 27), AWLCCLN (SEQ ID NO: 25), NWLCCLA (SEQ ID NO: 26), FWFCGAK (SEQ ID NO: 45), FWFCGAA (SEQ ID NO: 46), NWACCLN (SEQ ID NO: 47), NWLACLN (SEQ ID NO:48), AWACCLN (SEQ ID NO: 49), AWLACLN (SEQ ID NO: 50), AWL-CCLA (SEQ ID NO: 51), NWAACLN (SEQ ID NO: 52), NWACCLA (SEQ ID NO: 53), NWLACLA (SEQ ID NO: 54), AWAACLN (SEQ ID NO: 55), AWACCLA (SEQ ID NO: 56), NWAACLA (SEQ ID NO: 58) and AWAACLA (SEQ ID NO: 59).

14. A polypeptide according to claim 13, in which said Rev protein is Rev protein of HIV-1, HIV-2, SIV, SHIV or FIV.

15. A polypeptide according to claim 13, in which said heptapeptide is capable of interacting with Rev protein of HIV-1 in a two-hybrid yeast test and in which said polypeptide is capable of inhibiting replication of the HIV-1 virus in vivo.

16. A population of interaction molecules, each member of the population being constituted by or comprising a polypeptide, said polypeptide comprising the following elements:
  (a) a heptapeptide motif with the sequence $X_1X_2X_3X_4X_5X_6X_7$; in which $X_1$, $X_2$, $X_3$, $X_4$, $X_5$, $X_6$ and $X_7$ are amino acids independently selected from natural or modified amino acids,
  (b) a transduction domain; and
  (c) a stabilization domain which is a fragment of ubiquitin or SUMO-1, the amino acid sequence of which fragment comprises SEQ ID NO:1 or SEQ ID NO:15;
characterized in that it is a chimeric polypeptide, in that the amino acid $X_7$ is 5 to 35 amino acids from the C-terminal end of said polypeptide, in that domain (b) is located C-terminally with respect to motif (a), and in that the stabilization domain (c) is located N-terminally with respect to the heptapeptide motif of said polypeptide and each member of the population being distinguished from other members by the heptapeptide sequence alone.

17. A population of interaction molecules according to claim 16, characterized in that said population comprises at least 100 distinct molecules.

18. A population of interaction molecules according to claim 16, characterized in that each member comprises the following sequence:
$X_1X_2X_3X_4X_5X_6X_7$PGKKRRQRRRG (SEQ ID NO: 6).

19. A population of interaction molecules according to claim 16, characterized in that each member comprises the following sequence:
MSDQEAKPSTEDLGDKKEGEYIKLKVIGQDSSEIH-FKVKMTTHLKKLKESYCQRQGVPMNSLRFLFE-GQRIADNHTPKELGMEEEDVIEVYQEQTARPPN-PKKEIELGGGGSX$_1$X$_2$X$_3$X$_4$X$_5$X$_6$X$_7$PGKKRRQRR-RG (SEQ ID NO: 7), or each member comprises the following sequence: MSDQEAKPSTEDLGDKKEG-EYIKLKVIGQDSSEIHFKVKMTHLKKLKESYCQ-RQGVPMNSLRFLFEGQRIADNHTPKELGMEEE-DVIEVYQEQTARGGGGSX$_1$X$_2$X$_3$X$_4$X$_5$X$_6$X$_7$PGK-KRRQRRRG (SEQ ID NO: 78).

* * * * *